US009095328B2

(12) United States Patent
Headley, Jr. et al.

(10) Patent No.: US 9,095,328 B2
(45) Date of Patent: Aug. 4, 2015

(54) ENDOSCOPES HAVING MULTIPLE LUMENS FOR TISSUE ACQUISITION AND REMOVAL AND RELATED METHODS OF USE

(75) Inventors: F. Anthony Headley, Jr., Plymouth, MN (US); Robert B. DeVries, Northborough, MA (US); Kenneth Blair, Burlington, MA (US); James Weldon, Newton Center, MA (US); Adam Cohen, Arlington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 924 days.

(21) Appl. No.: 12/617,083

(22) Filed: Nov. 12, 2009

(65) Prior Publication Data
US 2010/0152612 A1 Jun. 17, 2010

Related U.S. Application Data

(60) Provisional application No. 61/193,658, filed on Dec. 12, 2008.

(51) Int. Cl.
| A61B 10/00 | (2006.01) |
| A61B 1/00 | (2006.01) |
| A61B 1/12 | (2006.01) |
| A61B 17/24 | (2006.01) |
| A61B 17/26 | (2006.01) |
| A61B 10/04 | (2006.01) |
| A61B 17/221 | (2006.01) |
| A61B 17/22 | (2006.01) |
| A61B 1/018 | (2006.01) |
| A61B 10/02 | (2006.01) |
| A61B 10/06 | (2006.01) |
| A61B 17/30 | (2006.01) |

(52) U.S. Cl.
CPC ............. *A61B 10/04* (2013.01); *A61B 1/018* (2013.01); *A61B 10/0283* (2013.01); *A61B 10/06* (2013.01); *A61B 17/22* (2013.01); *A61B 17/221* (2013.01); *A61B 17/22031* (2013.01); *A61B 2010/0225* (2013.01); *A61B 2017/306* (2013.01)

(58) Field of Classification Search
CPC ........ A61B 1/018; A61B 10/04; A61B 10/06; A61B 17/22; A61B 17/22031; A61B 17/221; A61B 17/32056
USPC ......... 600/104, 117, 129, 153, 156, 562–566; 604/104, 118, 164.01, 164.02, 164.09, 604/264; 606/106, 110, 113–115, 205
See application file for complete search history.

(56) References Cited

U.S. PATENT DOCUMENTS

| 5,190,555 | A | * | 3/1993 | Wetter et al. | 606/114 |
| 5,373,854 | A | * | 12/1994 | Kolozsi | 600/562 |
| 5,423,830 | A | * | 6/1995 | Schneebaum et al. | 606/115 |
| 5,458,112 | A | | 10/1995 | Weaver | |
| 5,573,008 | A | | 11/1996 | Robinson et al. | |
| 5,636,639 | A | | 6/1997 | Turturro et al. | |
| 5,645,075 | A | | 7/1997 | Palmer et al. | |
| 5,746,216 | A | | 5/1998 | Turturro et al. | |
| 5,797,957 | A | | 8/1998 | Palmer et al. | |
| 5,840,043 | A | | 11/1998 | Palmer et al. | |
| 5,895,361 | A | | 4/1999 | Turturro | |
| 5,897,507 | A | | 4/1999 | Kortenbach et al. | |
| 5,967,997 | A | | 10/1999 | Turturro et al. | |

(Continued)

*Primary Examiner* — Devin Henson
(74) *Attorney, Agent, or Firm* — Bookoff McAndrews, PLLC

(57) ABSTRACT

Embodiments of the invention include an endoscope including multiple lumens for tissue acquisition and removal and related methods of use.

36 Claims, 17 Drawing Sheets

(56) References Cited

U.S. PATENT DOCUMENTS

| | | | |
|---|---|---|---|
| 6,099,483 A | 8/2000 | Palmer et al. | |
| 6,123,678 A | 9/2000 | Palmer et al. | |
| 6,142,956 A | 11/2000 | Kortenbach et al. | |
| 6,174,292 B1 | 1/2001 | Kortenbach et al. | |
| 6,193,671 B1 | 2/2001 | Turturro et al. | |
| 6,331,165 B1 | 12/2001 | Turturro et al. | |
| 6,461,310 B1 | 10/2002 | Palmer et al. | |
| 6,537,205 B1 * | 3/2003 | Smith | 600/104 |
| 6,544,194 B1 | 4/2003 | Kortenbach et al. | |
| 6,561,988 B1 | 5/2003 | Turturro et al. | |
| 6,832,990 B2 | 12/2004 | Kortenbach et al. | |
| 6,926,676 B2 | 8/2005 | Turturro et al. | |
| 6,951,568 B1 * | 10/2005 | Chin | 606/190 |
| 6,958,069 B2 * | 10/2005 | Shipp et al. | 606/127 |
| 6,971,988 B2 * | 12/2005 | Orban, III | 600/104 |
| 7,094,245 B2 | 8/2006 | Adams et al. | |
| 7,204,811 B2 | 4/2007 | Kortenbach et al. | |
| 7,297,121 B2 | 11/2007 | Turturro et al. | |
| 7,347,828 B2 | 3/2008 | Francese et al. | |
| 7,396,329 B2 * | 7/2008 | Nakao | 600/204 |
| 7,846,107 B2 * | 12/2010 | Hoffman et al. | 600/561 |
| 8,075,510 B2 * | 12/2011 | Aklog et al. | 604/6.11 |
| 8,216,234 B2 * | 7/2012 | Long | 606/50 |
| 8,372,000 B2 * | 2/2013 | Weisman | 600/104 |
| 2002/0029006 A1 | 3/2002 | Turturro et al. | |
| 2002/0107457 A1 | 8/2002 | Francese et al. | |
| 2003/0069592 A1 | 4/2003 | Adams et al. | |
| 2003/0073928 A1 | 4/2003 | Kortenbach et al. | |
| 2004/0243024 A1 | 12/2004 | Kortenbach et al. | |
| 2005/0107809 A1 | 5/2005 | Litscher et al. | |
| 2005/0119652 A1 | 6/2005 | Vetter et al. | |
| 2005/0137591 A1 * | 6/2005 | Barry et al. | 606/45 |
| 2005/0182426 A1 | 8/2005 | Adams et al. | |
| 2005/0197536 A1 | 9/2005 | Banik et al. | |
| 2005/0245841 A1 | 11/2005 | Turturro et al. | |
| 2006/0069311 A1 | 3/2006 | Sullivan et al. | |
| 2006/0084885 A1 | 4/2006 | Reydel | |
| 2006/0106281 A1 | 5/2006 | Boulais et al. | |
| 2006/0106285 A1 | 5/2006 | Boulais et al. | |
| 2006/0173244 A1 | 8/2006 | Boulais et al. | |
| 2007/0270709 A1 | 11/2007 | Kortenbach et al. | |
| 2008/0221437 A1 | 9/2008 | Agro et al. | |
| 2008/0312496 A1 * | 12/2008 | Zwolinski | 600/104 |

* cited by examiner

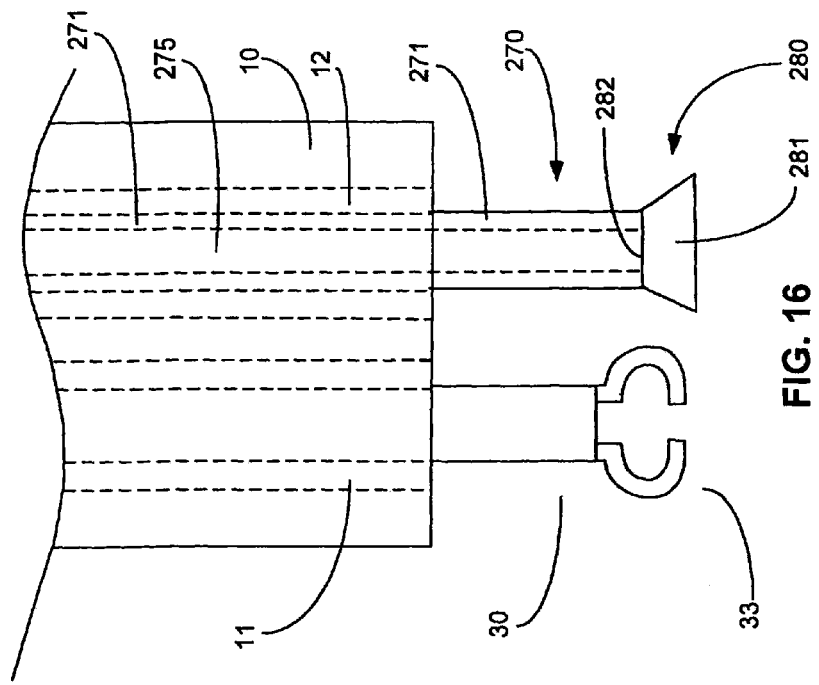
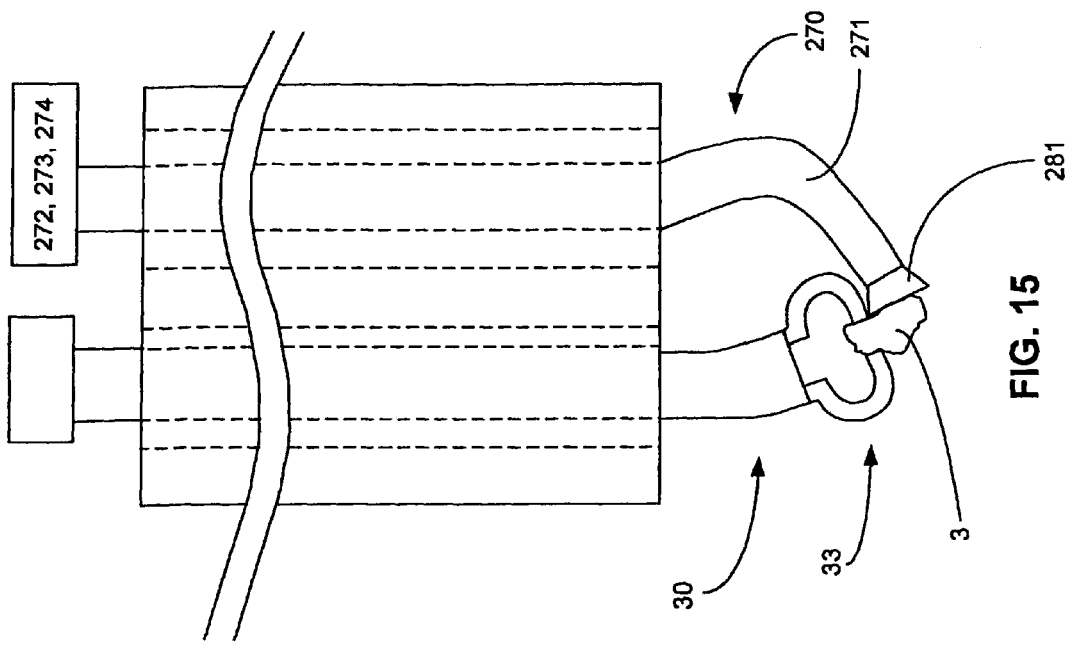

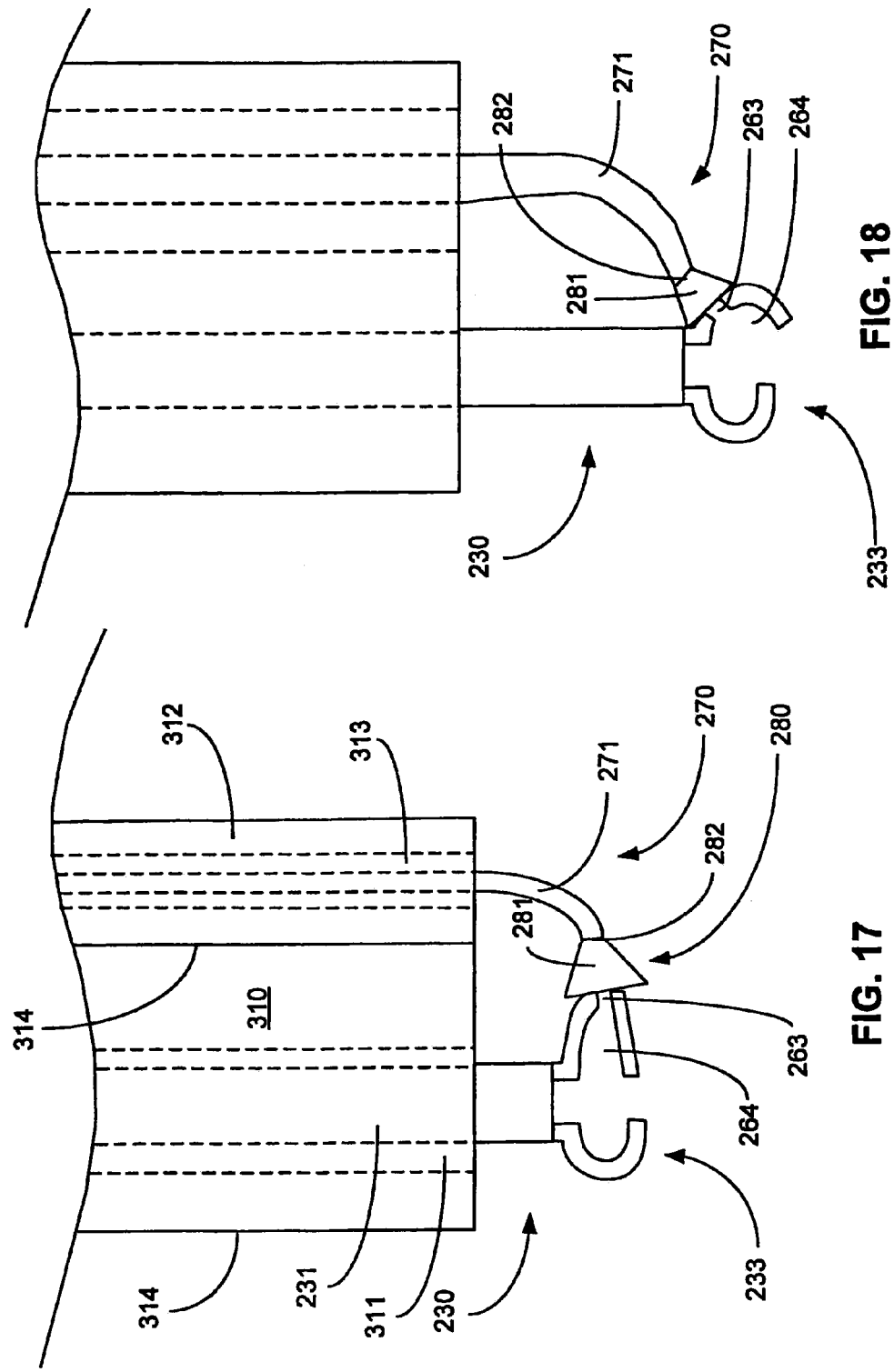

ENDOSCOPES HAVING MULTIPLE LUMENS FOR TISSUE ACQUISITION AND REMOVAL AND RELATED METHODS OF USE

CROSS-REFERENCE TO RELATED APPLICATION

This patent application claims the benefit of priority under 35 U.S.C. §119 to U.S. Provisional Patent Application No. 61/193,658, entitled ENDOSCOPES HAVING MULTIPLE LUMENS FOR TISSUE ACQUISITION AND REMOVAL AND RELATED METHODS OF USE, filed Dec. 12, 2008, the entirety of which is incorporated herein by reference.

DESCRIPTION OF THE INVENTION

1. Field of the Invention

Embodiments of the invention include an endoscope including multiple lumens for tissue acquisition and removal and related methods of use.

2. Background of the Invention

Tissue samples sometimes need to be acquired from the body to perform diagnostic tests so as to determine whether tissue is diseased. To that end, a biopsy forceps instrument may be advanced into a body lumen, sever a tissue sample, store the tissue sample in the forceps jaw, and then the biopsy forceps instrument may be advanced out of the body lumen where the tissue sample may be removed from the forceps jaw. The procedure is then repeated as many times as necessary until the desired number of tissue samples have been acquired.

SUMMARY OF THE INVENTION

An embodiment of the invention may include an apparatus. The apparatus may include an endoscope including a first lumen and a second lumen, and a tissue acquisition device disposed in the first lumen and a tissue removal device disposed in the second lumen. The tissue acquisition device and the tissue removal device may be configured to be moveable relative to the endoscope. The tissue acquisition device may be configured to acquire a tissue sample from a body lumen and the tissue removal device may be configured to remove the tissue sample from the tissue acquisition device.

Various embodiments of the invention may include one or more of the following aspects: the tissue acquisition device may be a biopsy forceps; the tissue removal device may define a suction lumen configured to suction the tissue sample from the biopsy forceps; the tissue acquisition device may define a fluid lumen for flow communication with a source of fluid, and the fluid lumen may be configured to accommodate fluid flow to dislodge the tissue sample from the tissue acquisition device; the tissue acquisition device may include at least one jaw defining a cavity, and the fluid lumen may be configured to accommodate fluid flow to dislodge the tissue sample from the cavity; an elongate member may be disposed in the first lumen, the elongate member may define a working lumen and a fluid lumen, the tissue acquisition device may be disposed in the working lumen and may be longitudinally moveable relative to the elongate member, and the fluid lumen for flow communication with a source of fluid and may be configured to accommodate fluid flow; the fluid flow may be configured to dislodge a tissue sample from a distal assembly of the tissue acquisition device; the tissue acquisition device may include at least one jaw defining a cavity, and the fluid lumen of the elongate member may be configured to accommodate fluid flow to dislodge the tissue sample from the cavity; the tissue removal device may include an elongate member defining a suction lumen, the apparatus may further include a source of suction and a storage device, both of which may be in flow communication with the suction lumen; the tissue removal device may include a distal assembly including a flexible portion that may extend radially and distally away from the distal assembly, the flexible portion surrounding a distal end of the suction lumen, and the suction lumen may be configured to suction the tissue sample from the tissue acquisition device to the storage device; the flexible portion may be configured to form a substantially airtight seal with at least one of an outer surface of the endoscope and a storage device of the tissue acquisition device; the at least one of the source of suction and the storage device may be located outside of the body lumen; the tissue removal device may include an expandable distal assembly configured to be in a collapsed configuration in the second lumen and in an expanded configuration in the body lumen, the expandable distal assembly may be configured to accommodate both the tissue sample and a distal assembly of the tissue acquisition device in the expanded configuration, and the suction lumen may be configured to suction the tissue sample from the expandable distal assembly to the storage device; the expandable distal assembly may be self-expanding; the expandable distal assembly may include an expandable portion defining a cavity configured to accommodate both the tissue sample and the distal assembly of the tissue acquisition device, and a collapsible rim defining a proximal edge of the expandable portion; the expandable distal assembly may further include a collapsible member connected to the collapsible rim and the elongate member; the elongate portion of the tissue removal device and the second lumen may be configured to prevent rotational movement relative to each other; the elongate portion of the tissue removal device and the second lumen may be keyed; the elongate portion of the tissue removal device and the second lumen may have corresponding geometric configurations; the elongate portion of the tissue removal device and the second lumen may have substantially the same cross-sectional shape; and the opening of the cavity, configured to allow passage of both the tissue sample and the distal assembly of the acquisition device therethrough, may be disposed on a proximal portion of the expandable portion.

An embodiment of the invention may include a method. The method may include providing an endoscope including a first lumen and a second lumen, advancing the endoscope into a body lumen, advancing a tissue acquisition device through the first lumen, and advancing a tissue removal device through the second lumen. The method may also include acquiring a tissue sample from the body lumen using the tissue acquisition device, removing the tissue sample from the tissue acquisition device to the tissue removal device via a lumen defined by the tissue removal device, and removing the tissue sample from the body lumen by proximally advancing the tissue sample through the lumen of the tissue removal device.

Various embodiments of the invention may include one or more of the following aspects: the tissue acquisition device may be a biopsy forceps; the lumen of the tissue removal device may be configured to accommodate one of fluid flow and suction to remove the tissue sample from the biopsy forceps; the method may further include placing the tissue sample in a distal assembly of the tissue acquisition device and providing fluid via a fluid lumen of the tissue acquisition device to the distal assembly so as to dislodge the tissue sample from the distal assembly and to the tissue removal device; the distal assembly may include at least one jaw defining a cavity, the method may further include acquiring the tissue sample by placing the tissue sample in the cavity and after placing the tissue sample in the cavity, dislodging the tissue sample from the cavity via the fluid from the fluid lumen; the tissue acquisition device may be disposed in a working lumen of the elongate member and may be moveable relative to the elongate member, the method may further include placing the tissue sample in a distal assembly of the tissue acquisition device and providing fluid via a fluid lumen of the elongate member to the distal assembly; the fluid may be configured to dislodge the tissue sample from the distal assembly; the distal assembly may include at least one jaw defining a cavity, the method may further include acquiring the tissue sample by disposing the tissue sample in the cavity and, after disposing the tissue sample in the cavity, dislodging the tissue sample from the cavity via the fluid from the fluid lumen of the elongate member; the tissue removal device may include a distal assembly including a flexible portion surrounding a distal end of the suction lumen, and the method may further include placing at least a portion of the tissue sample in an opening defined by the flexible portion; the tissue removal device may include a distal assembly including a flexible portion surrounding a distal end of the suction lumen, and the method may further include disposing the tissue sample in a storage chamber of the tissue acquisition device, placing the flexible portion around an aperture of the storage chamber, and, after placing the flexible portion around the aperture, removing the tissue sample from the storage chamber by suctioning the tissue sample through the aperture, into a distal end of the suction lumen, and into a storage device located outside of the body lumen; the tissue removal device may include a distal assembly surrounding a distal end of the suction lumen, and the method may further include retracting the distal assembly including the tissue sample into the first lumen, releasing the tissue sample from the distal assembly into the first lumen, placing the distal assembly around an external aperture of an auxiliary lumen in flow communication with the first lumen, and removing the tissue sample from the first lumen by suctioning the tissue sample through the auxiliary lumen, into a distal end of the suction lumen, and into a storage device located outside of the body lumen; the method may further include, after the step of acquiring the tissue sample, acquiring another tissue sample from the body lumen using the tissue acquisition device without removing the tissue acquisition device from the body lumen; the method may further include, after the step of suctioning the tissue sample, suctioning the other tissue sample from the tissue acquisition device to the tissue removal device via the suction lumen defined by the tissue removal device without removing the tissue removal device from the body lumen; and the method may further include, after the step of removing the tissue sample, removing the other tissue sample from the body lumen by proximally advancing the other tissue sample through the suction lumen of the tissue removal device without removing the tissue removal device from the body lumen.

An embodiment of the invention may include a tissue removal device. The tissue removal device may include an elongate member defining a suction lumen configured to be in flow communication with a source of suction. The tissue removal device may also include an expandable distal assembly coupled to the elongate member and configured to be in a collapsed configuration in a lumen of an endoscope and in an expanded configuration in a body lumen. The expandable distal assembly may be configured to accommodate both a tissue sample and a distal assembly of a tissue acquisition device in the expanded configuration. The suction lumen may be configured to suction the tissue sample from the expandable distal assembly via the suction lumen.

Various embodiments of the invention may include one or more of the following aspects: the expandable distal assembly may be self-expanding; the tissue removal device may further include a storage device in flow communication with the suction lumen, and at least one of the source of suction and the storage device may be located outside of the body lumen; the expandable distal assembly may include an expandable portion defining a cavity configured to accommodate both the tissue sample and the distal assembly of the tissue acquisition device, and a collapsible rim defining a proximal edge of the expandable portion; the expandable distal assembly may further include a collapsible member connected to the collapsible rim and the elongate member; the elongate member of the tissue removal device and the lumen of the endoscope may be configured to prevent rotational movement relative to each other; the elongate member of the tissue removal device and the lumen may be keyed; the elongate member of the tissue removal device and the lumen of the endoscope may have corresponding geometric configurations; the elongate member of the tissue removal device and the lumen of the endoscope may have substantially the same cross-sectional shape; an opening of the cavity, configured to allow passage of both the tissue sample and the distal assembly of the acquisition device therethrough, may be disposed on a proximal portion of the expandable portion; an apparatus including an endoscope including a lumen and the tissue removal device may be disposed in the lumen of the endoscope and may be moveable relative to the endoscope; and the endoscope may include a second lumen different from the lumen, the apparatus may further include the tissue acquisition device, the tissue acquisition device may be disposed in the second lumen of the endoscope, and the tissue acquisition device may be moveable relative to the endoscope.

An embodiment of the invention may include a method. The method may include providing an endoscope including a first lumen and a second lumen, advancing the endoscope into a body lumen, advancing a tissue acquisition device through the first lumen, and advancing a tissue removal device through the second lumen, a distal assembly of the tissue removal device may be advanced through the second lumen in a collapsed configuration. The method may further include expanding the distal assembly into an expanded configuration when the distal assembly exits a distal end of the second lumen, acquiring a tissue sample from the body lumen using the tissue acquisition device, placing a distal portion of the tissue acquisition device and the tissue sample in the distal assembly of the tissue removal device, and removing the tissue sample from the distal assembly by suctioning the tissue sample from the distal assembly.

Various embodiments of the invention may include one or more of the following aspects: the distal assembly may include an expandable portion defining a cavity configured to accommodate both the tissue sample and the distal assembly of the tissue acquisition device, and a collapsible rim defining a proximal edge of the expandable portion, and the method may further include expanding each of the expandable portion and the collapsible rim as they each individually exit the distal end of the second lumen; the distal assembly may further include a collapsible member connected to the collapsible rim and the elongate member; collapsing each of the expandable portion and the collapsible rim as they each individually enter the distal end of the second lumen; collapsing each of the expandable portion, the collapsible rim, and the collapsible member as they each individually enter the distal end of the second lumen; rotating the distal assembly so as to allow the tissue acquisition device and the tissue sample to be placed in the distal assembly; preventing the rotation of an elongate member of the tissue removal device relative to the second lumen; and placing the tissue sample and the distal portion of the tissue acquisition device through a proximal opening of the expandable portion.

An embodiment of the invention may include an apparatus. The apparatus may include an endoscope including a first lumen configured to accommodate a tissue acquisition device or a tissue removal device, an elongate member including a working lumen configured to accommodate the tissue acquisition device or the tissue removal device, one of the tissue acquisition device and the tissue removal device may be disposed in the first lumen and the other of the tissue removal device and the tissue acquisition device may be disposed in the working lumen, and both the tissue acquisition device and the tissue removal device may be moveable relative to the endoscope and the elongate member.

Various embodiments of the invention may include one or more of the following aspects: the elongate member may be attached to the endoscope at least along a portion of its length; and the elongate member may be completely unattached to the endoscope.

An embodiment of the invention may include a method. The method may include providing an endoscope including a first lumen configured to accommodate a tissue acquisition device or a tissue removal device, providing an elongate member including a working lumen configured to accommodate the tissue acquisition device or the tissue removal device, advancing the endoscope into a body lumen, advancing the elongate member into the body lumen. The method may further include advancing one of the tissue acquisition device and the tissue removal device through the first lumen, advancing the other of the tissue removal device and the tissue acquisition device through the working lumen, acquiring a tissue sample from the body lumen using the tissue acquisition device, and, within the body lumen, transferring the tissue from the tissue acquisition device to the tissue removal device. The method may also include removing the tissue sample from the body lumen.

Various embodiments of the invention may include one or more of the following aspects: the elongate member may be attached to the endoscope at least along a portion of its length; and the elongate member may be completely unattached to the endoscope.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 15 is a schematic view of an apparatus, according to still another embodiment of the invention;

FIG. 16 is a schematic view of the apparatus of FIG. 15;

FIG. 17 is a schematic view of an apparatus including the tissue acquisition device of FIG. 14, according to a still further embodiment of the invention;

FIG. 18 is a schematic view of an apparatus including the tissue acquisition device of FIG. 14, according to another embodiment of the invention.

DESCRIPTION OF THE EMBODIMENTS

Figure 1:
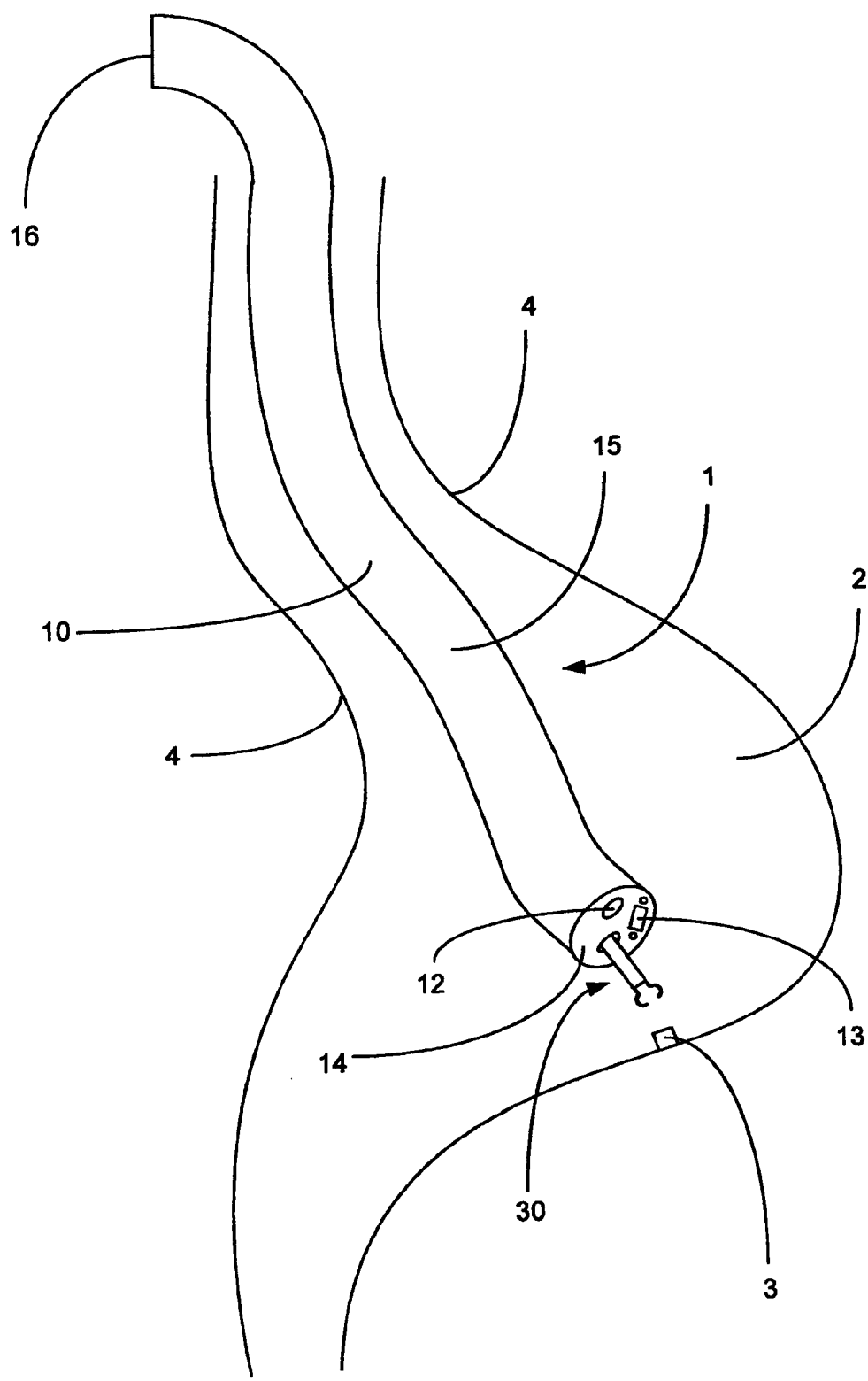
FIG. 1 is a schematic view of an apparatus disposed in a body lumen, according to an exemplary embodiment of the invention.
Figure 2:
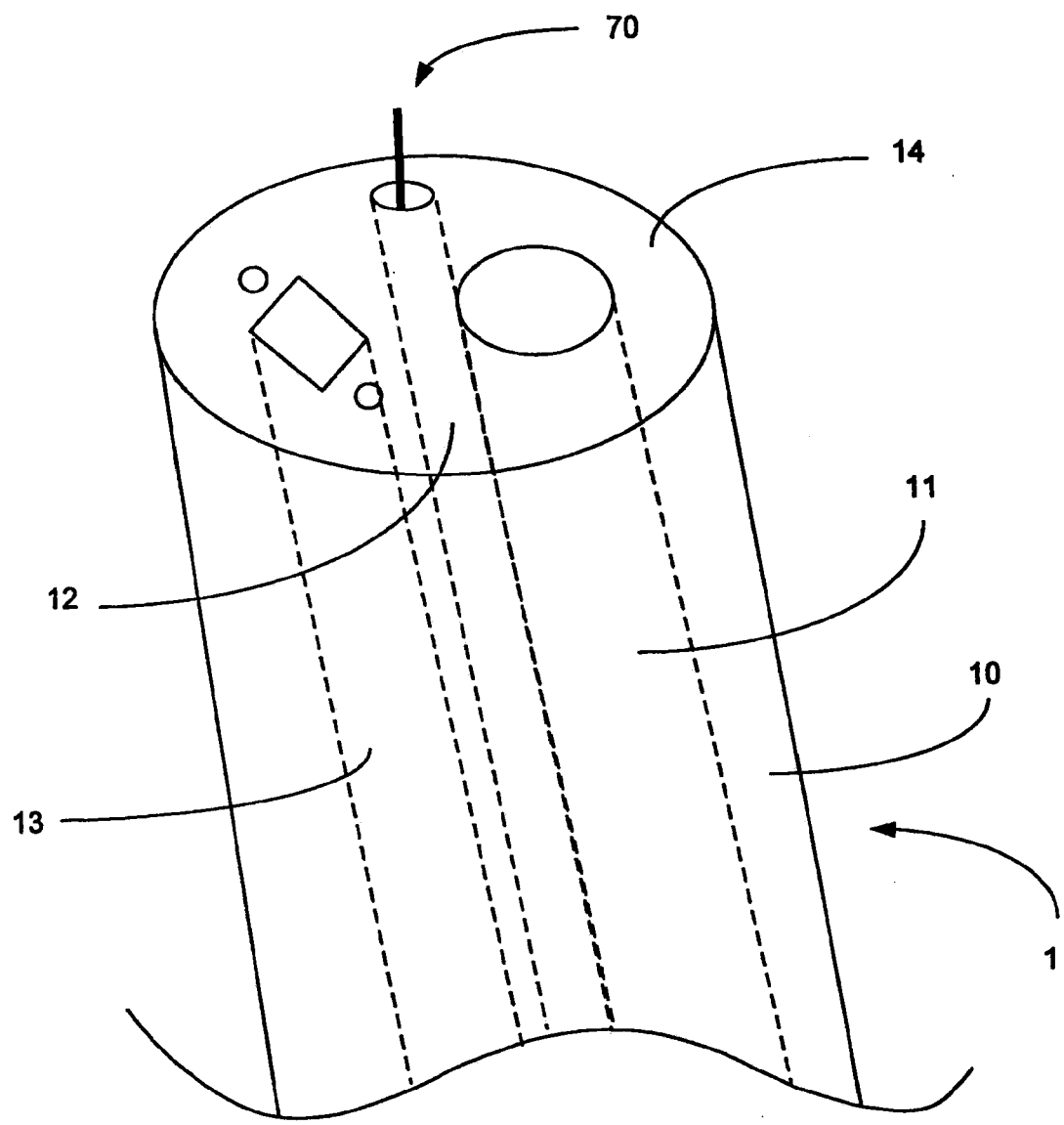
FIG. 2 is a schematic view of a distal portion of the apparatus depicted in FIG. 1.

Reference will now be made in detail to exemplary embodiments of the invention, examples of which are illustrated in the accompanying drawings. Wherever possible, the same reference numbers will be used throughout the drawings to refer to the same or like parts.

Embodiments of the invention may include an apparatus 1. Apparatus 1 may include an endoscope 10, a tissue acquisition device 30, and a tissue retrieval device 70, for example, as set forth in FIGS. 1-4.

While the embodiments discussed below are disclosed in connection with an endoscope (e.g., endoscope 10), any suitable device, such as, for example, a guide tube, trocar, or introducer, capable of introducing a tissue acquisition device and/or a tissue removal device into a patient may be used in connection with the described embodiments.

Endoscope 10 may be configured to be advanced through any body lumen, for example, GI tract 2. Endoscope 10 may have a distal end 14 and proximal end 16. Endoscope 10 may be made out of any suitable material, for example, a suitable biocompatible material configured to be advanced through GI tract 2.

Endoscope 10 may include an outer housing 15 defining multiple lumens extending therethrough, for example, first lumen 11, second lumen 12, and third lumen 13. Although the depicted embodiment of endoscope 10 includes three lumens, endoscope 10 may include a greater or lesser number of lumens. Lumens 11, 12, 13 may have any suitable length, size, cross-sectional area, shape, and/or configuration, and may extend along at least a portion of the length of endoscope 10. For example, first lumen 11 and second lumen 12 may extend substantially along the entire length of endoscope 10 and may have a substantially circular shape with first lumen 11 having a larger cross-sectional area than second lumen 12.

One or more of lumens 11, 12, 13 may be configured to accommodate one or more medical devices extending therethrough. For example, first lumen 11 may be configured to accommodate tissue acquisition device 30, and second lumen 12 may be configured to accommodate tissue retrieval device 70.

One of lumens 11, 12, 13 may be configured to accommodate any suitable visual device. For example, third lumen 13 may have a substantially rectangular cross-sectional shape and may be configured to contain a visual device allowing a user to view an area distal to distal end 14 of endoscope 10. The visual device may be built into endoscope 10, and include one or more of a light source, lens, fiber optics, and/or any suitable electronic vision components known in the art, etc., to view a work site within a patient's body lumen.

Tissue acquisition device 30 may be any suitable medical device configured to acquire a tissue sample 3 from the body, for example, a biopsy forceps instrument configured to acquire tissue sample 3 from wall 4 of GI tract 2. Tissue acquisition device 30 may include an elongate member 31, a proximal handle portion 32, and a distal assembly 33. Proximal handle portion 32 may be connected to distal assembly 33 via elongate member 31, and may be configured to allow a user to manipulate distal assembly 33. For example, one or more wires may connect handle portion 32 to distal assembly 33 via a lumen of elongate member 31.

Distal assembly 33 may have any suitable configuration to sever and at least temporarily store tissue sample 3. For example, distal assembly 33 may include a first jaw 40 and a second jaw 50. Each of jaws 40, 50 may include a respective edge 41, 51 configured to come into contact with each other. One or both of edges 41, 51 may be configured to cut tissue, for example, by being sharp. One of edges 41, 51 may have a substantially flat surface such when edges 41, 51 are brought together, tissue caught between edges 41, 51 may be severed by pressure exerted between one edge 41, 51 being sharp and the other edge being substantially flat. Alternatively, one or both jaws 40, 50 may include teeth.

Each of jaws 40, 50 may be configured to store tissue. For example, one or more of jaws 40, 50 may include a cavity 42, 52 configured to store one or more tissue samples 3 severed from the body by edges 41, 51.

Tissue acquisition device 30 may be configured to be placed through first lumen 11 with distal assembly 33 in either an open or closed configuration. For example, first lumen 11 may have a cross-sectional area such that distal assembly 33 including jaws 40, 50 may be advanced therethrough in only a closed configuration.

Tissue removal device 70 may be any suitable device for removing tissue sample 3 from tissue acquisition device 30. For example, tissue removal device 70 may include any known device capable of facilitating the removal of tissue samples taken from within a patient's body. Tissue removal device 70 may include an elongate member 71, a proximal handle portion 72, a storage portion 74, and a distal assembly 80. Proximal handle portion 72 may be connected to distal assembly 80 via elongate member 71, and may be configured to allow a user to manipulate distal assembly 80. For example, one or more wires may connect handle portion 72 to distal assembly 80 via a lumen 73 of elongate member 71. Lumen 73 may also be in flow communication with proximal storage portion 74. Storage portion 74 may be configured to store one or more tissue samples. Although the depicted embodiments illustrate that storage portion 74 may be disposed at a proximal end of tissue removal device 70, storage portion 74 may be disposed anywhere along the length of tissue removal device 70.

Figure 3:
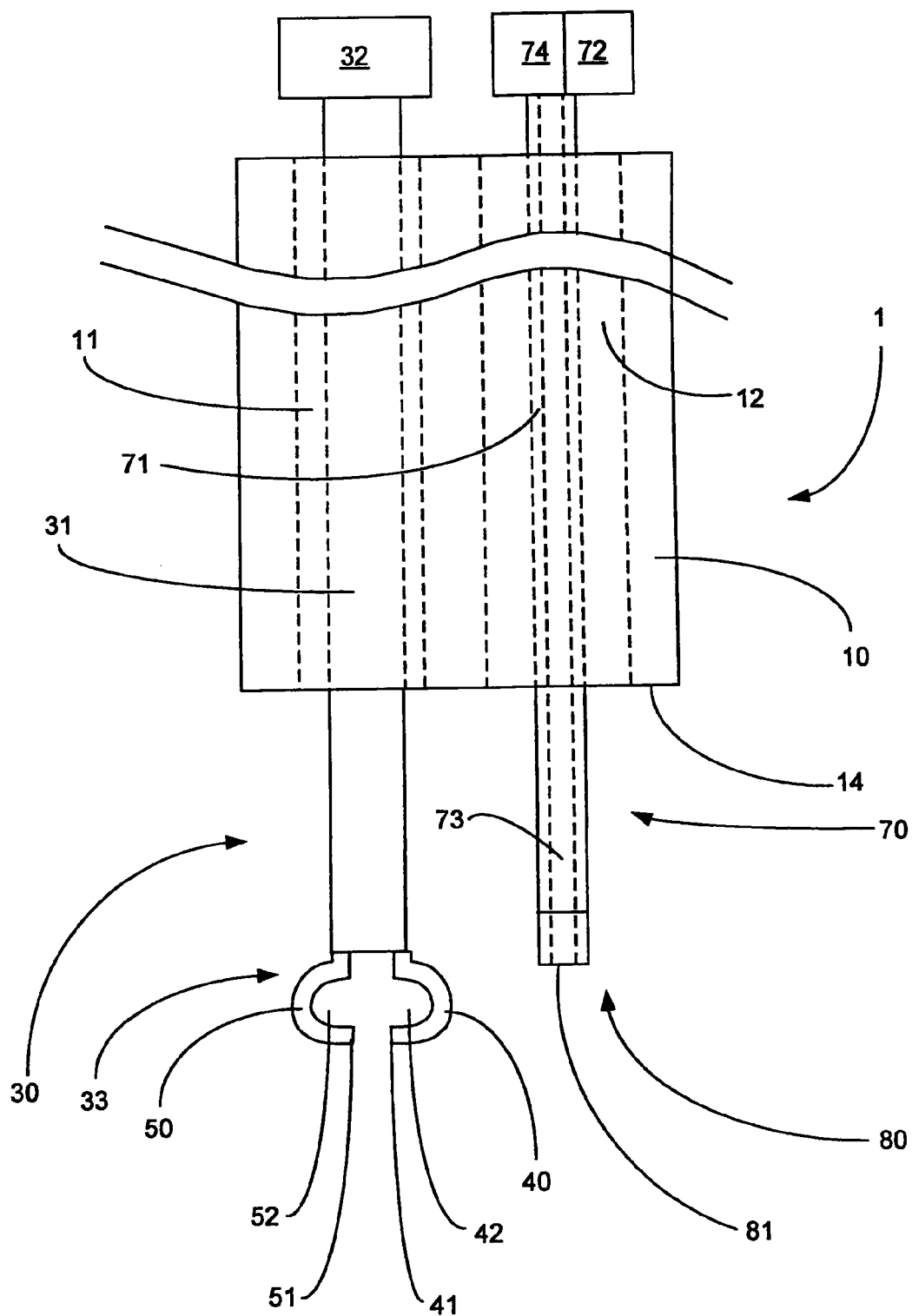
FIGS. 3-4 are various schematic views of the apparatus of FIG. 1.
Figure 4:
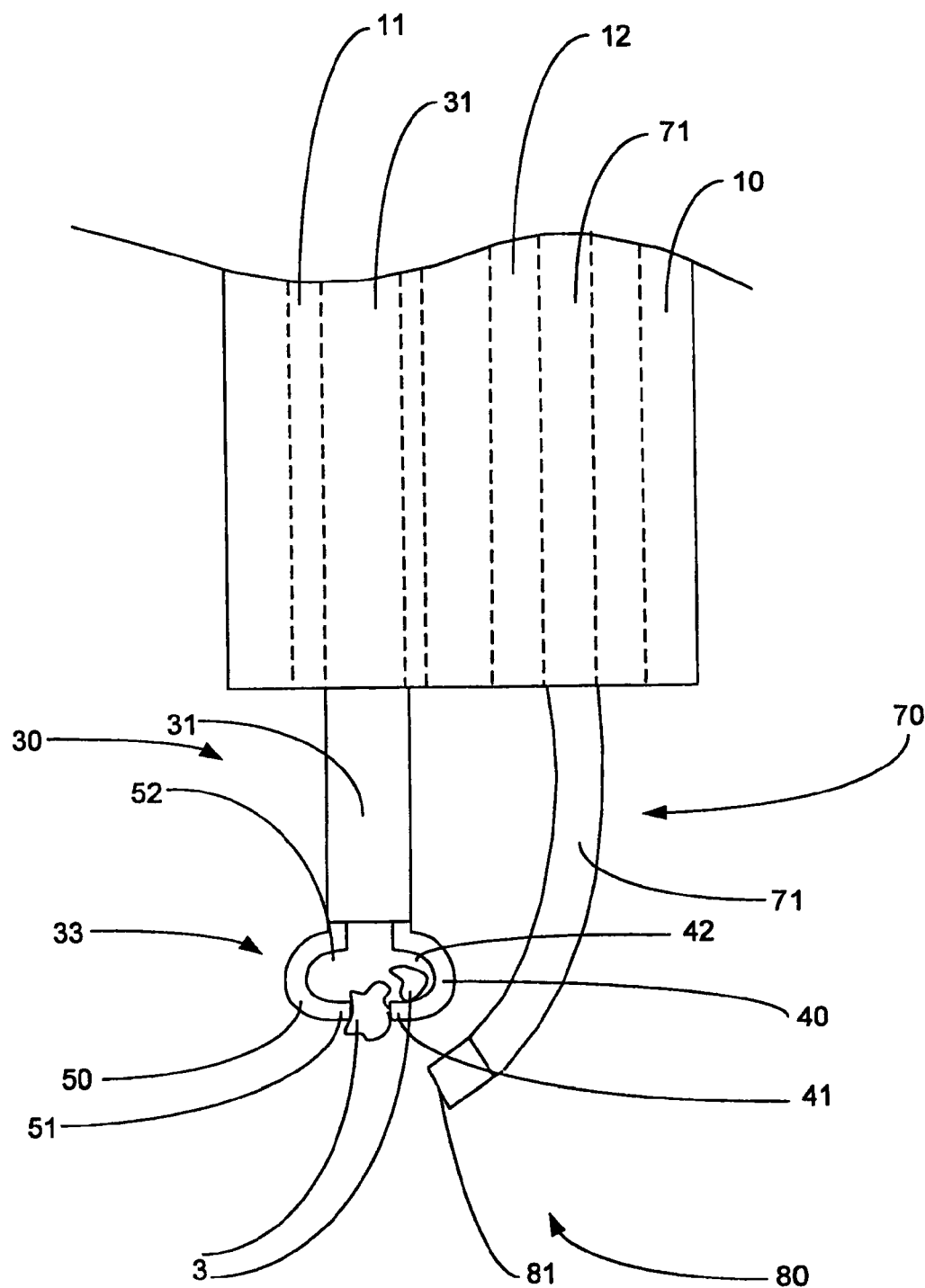

Distal assembly 80 may be any suitable assembly configured to remove tissue from distal assembly 33 of tissue acquisition device 30. For example, distal assembly 80 may include a suction portion 81, as shown in FIGS. 3-4. Suction portion 81 may be configured to suction tissue sample 3 into proximal storage portion 74 via lumen 73, for example, by placing suction portion 81 adjacent to tissue sample 3, suctioning tissue sample 3 into lumen 73, and thus removing tissue sample 3 from tissue acquisition device 30, for example, as set forth in FIG. 4. Suction portion 81 may be configured to remove at least one tissue sample 3 from tissue acquisition device 30 substantially simultaneously.

Once the desired number of tissue samples 3 have been suctioned out of tissue acquisition device 30 by suction portion 81 of distal assembly 80 into proximal storage portion 74 via lumen 73, distal assembly 80 may be advanced proximally from endoscope 10 via second lumen 12. Tissue samples 3 removed by tissue removal device 70 may be stored in proximal storage portion 74 or any other storage device for future analysis, diagnosis, and/or experimentation.

An embodiment of the invention may include a method of acquiring and removing multiple tissue samples 3, for example, using apparatus 1. Distal end 14 of endoscope 10 may be advanced through a body lumen, for example, GI tract 2.

Once distal end 14 is adjacent the desired location in GI tract 2, which may be ascertained using a visual device which may be disposed in third lumen 13, tissue acquisition device 30 may be advanced down first lumen 11 until distal assembly 33 emerges out of first lumen 11 and extends past distal end 14. Jaws 40, 50 may be in either an open or closed configuration at any point in time. Distal assembly 33 may be manipulated using handle portion 32 and/or elongate member 31.

Once a portion of wall 4 of GI tract 2 is identified as an area from which a tissue sample is desired, jaws 40, 50 may be opened and edges 41, 51 may be used to clamp and sever tissue from wall 4 of GI tract 2 so as to obtain tissue sample 3. At this point, tissue sample 3 may be stored in one or more of cavities 42, 52. Tissue acquisition device 30 may then be used to acquire one or more additional tissue samples 3, for example, until either the requisite number have been acquired or cavities 42, 52 can no longer accommodate further tissue samples 3.

Tissue removal device 70 may be advanced down second lumen 12 until distal assembly 80 emerges from second lumen 12 and extends past distal end 14 of endoscope 10. Distal assembly 80 may be in any suitable configuration.

Using the visual device in third lumen 13, distal assembly 80 may be manipulated using elongate member 71 and/or handle portion 72 and maneuvered adjacent to tissue acquisition device 30. Jaws 40, 50 of tissue acquisition device 30 may then be opened and suction portion 81 of distal assembly 80 may be placed adjacent to one or more tissue samples 3 disposed in cavities 42, 52. At least some of tissue samples 3 disposed in cavities 42, 52 may be suctioned into lumen 73 by suction portion 81 and then into proximal storage portion 74, for example, as shown in FIGS. 3 and 4.

Once the desired number of tissue samples have been suctioned into proximal storage portion 74 via lumen 73 and suction portion 81, tissue removal device 70 may be advanced proximally through second lumen 12 and then out of proximal end 16 of endoscope 10. The suctioned tissue samples 3 may be stored in proximal storage portion 74 of tissue removal device 70, or removed from tissue removal device 70 and may either be immediately analyzed or placed in storage for later analysis. Tissue acquisition device 30 may also be advanced proximally through first lumen 11 and then out of proximal end 16 of endoscope 10.

In some embodiments, tissue removal device 70 may be used to aid in acquiring tissue. For example, tissue removal device 70 may assist in holding targeted tissue stationary while tissue acquisition device 30 acquires the targeted tissue. Tissue removal device 70 may hold targeted tissue by any suitable means known in the art. For example, tissue removal device 70 may be used to mechanically brace, position, and/or pin targeted tissue. Alternatively, tissue removal device 70 may use suction to hold targeted tissue in place for acquisition by tissue acquisition device 30.

Any of the method steps set forth herein may be repeated in any order or combination as many times as desired until the desired number of tissue samples 3 have been acquired. Once that has occurred, tissue acquisition device 30 and tissue removal device 70 may be removed from GI tract 2 separately from or together with endoscope 10.

Apparatus 1 and its related methods may have several advantages. For example, tissue removal device 70 may remove tissue samples 3 from tissue acquisition device 30 without removing tissue acquisition device 30 or tissue removal device 70 from GI tract 2. Tissue acquisition device 30 may be used to acquire multiple tissue samples 3. Apparatus 1 and related methods therefore reduce the time, expense, and/or patient trauma due to the tissue acquisition procedures when multiple tissue samples 3 are desired.

Figure 5:
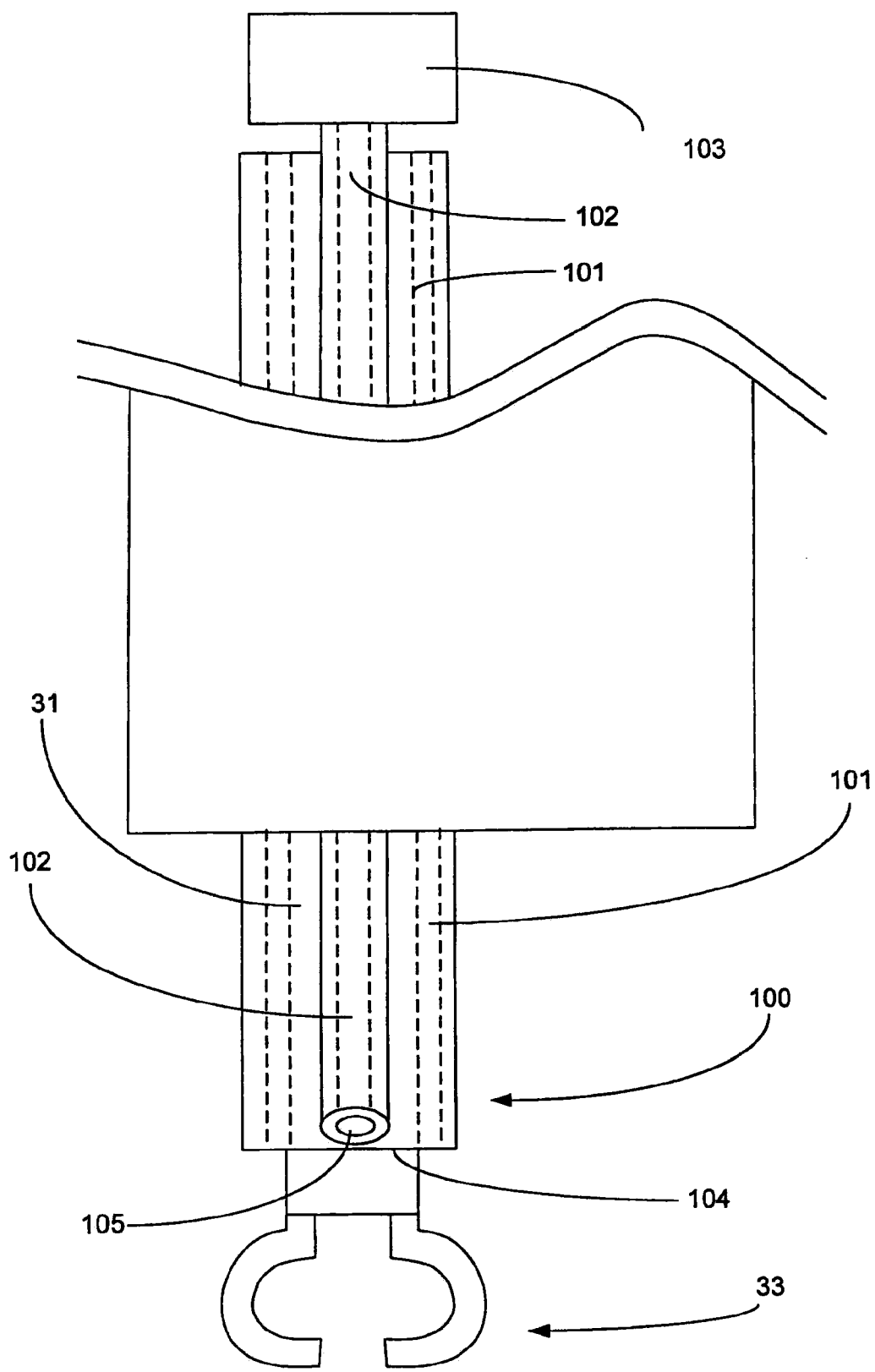
FIG. 5 is a schematic view of an apparatus including an elongate member, according to another embodiment of the invention.
Figure 6:
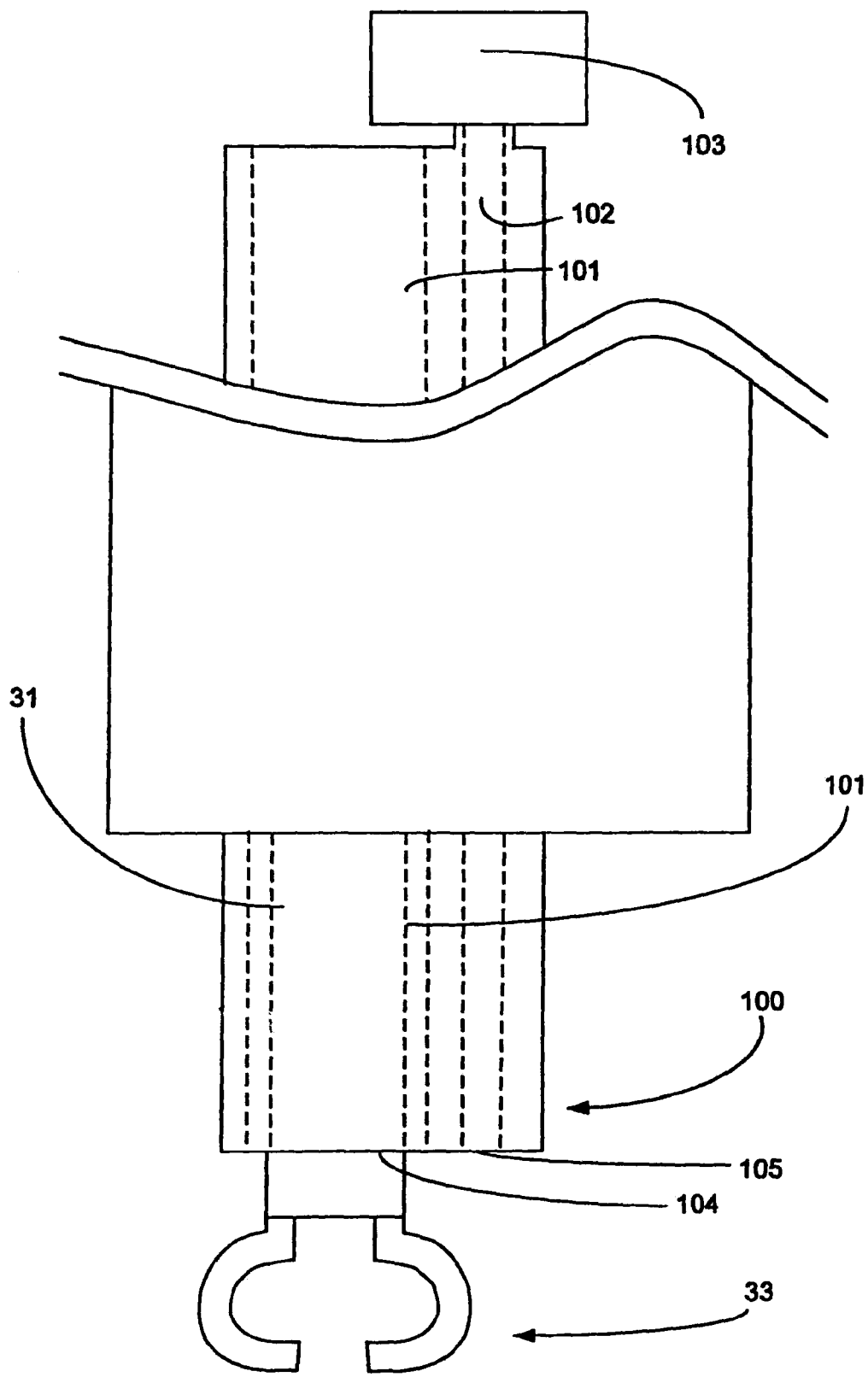
FIG. 6 is a schematic view of an apparatus including an elongate member, according to a further embodiment of the invention.

In another embodiment of the present invention, apparatus 1 may include an elongate member 100 connected to a source of fluid 103. Elongate member 100 may be a sheath that includes one or more lumens 101, 102. Although the depicted embodiment of elongate member 100 includes two lumens, elongate member 100 may include a greater or lesser number of lumens. Examples of elongate member 100 are shown in FIGS. 5 and 6.

First lumen 101 may be configured to accommodate any tissue acquisition device set forth herein, for example, elongate member 31 of tissue acquisition device 30. Distal end 104 of first lumen 101 may be positioned proximal to distal assembly 33.

Second lumen 102 may be configured to accommodate fluid flow therethrough, for example, from source of fluid 103. Distal end 105 of second lumen 102 may be configured and/or positioned to direct fluid flow at a portion of distal assembly 33, for example, inside cavities 42, 52 of jaws 40, 50. Such directed fluid flow may assist in dislodging tissue samples 3 from distal assembly 33 so as to allow them to be more easily placed on or in any tissue removal device set forth herein so as to be removed from GI tract 2. Second lumen 102 may be disposed on a separate portion of elongate member 100, as shown in FIG. 5, or may be an integral portion of elongate member 100, for example, as shown in FIG. 6.

Figure 7:
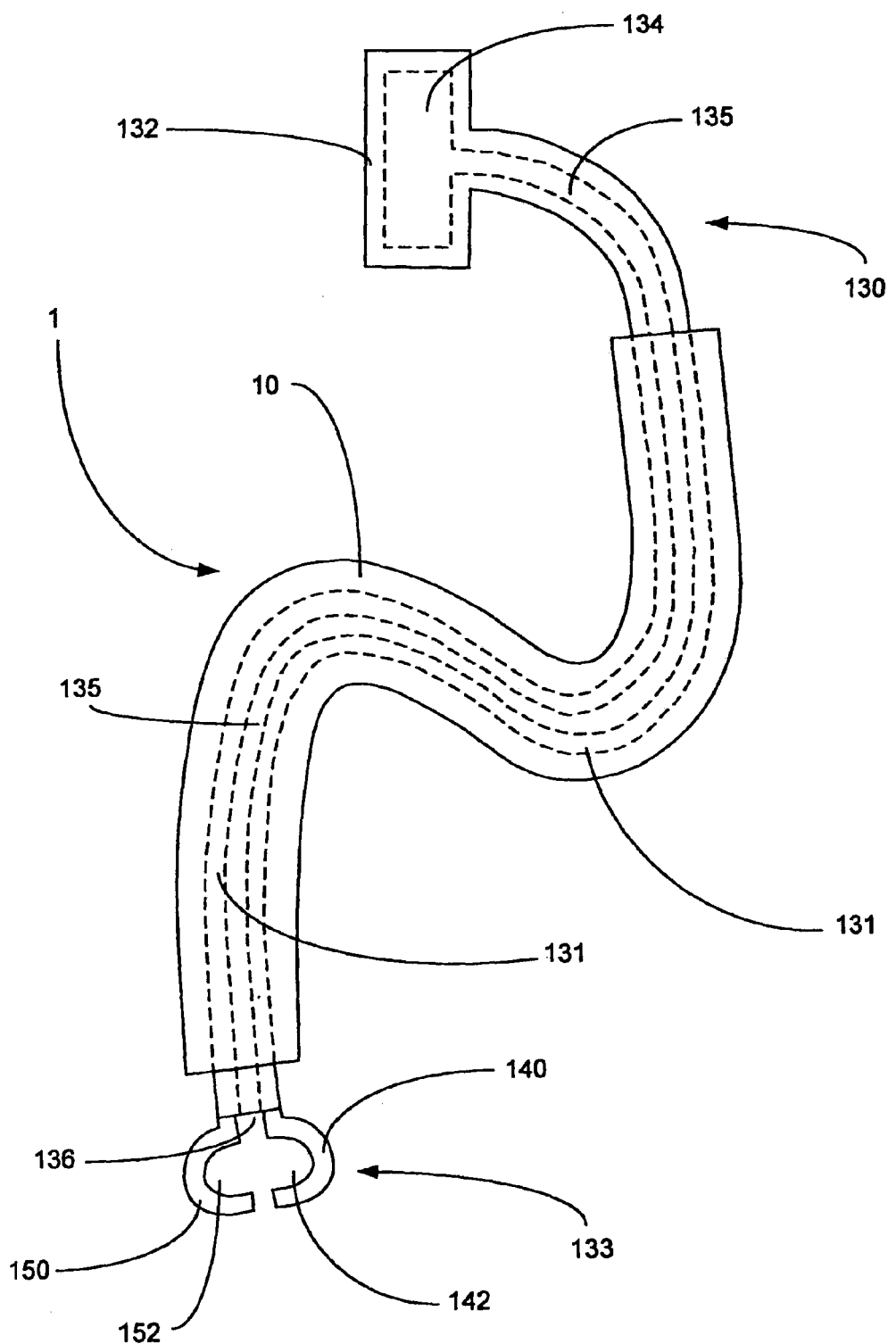
FIG. 7 is a schematic view of an apparatus, according to yet another embodiment of the invention.

According to another embodiment of the invention, apparatus 1 may include tissue acquisition device 130, for example, as shown in FIG. 7. Tissue acquisition device 130 may be used in place of any tissue acquisition device and related methods or method steps set forth herein. Tissue acquisition device 130 may include elongate member 131, handle portion 132, source of fluid 134, and distal assembly 133. Elongate member 131 may define a lumen 135 in flow communication with source of fluid 134 and/or distal assembly 133. Lumen 135 may be connected to source of fluid 134 via handle portion 132. Lumen 135 may be disposed with respect to distal assembly 133 so as to allow fluid from lumen 135 to assist in removing tissue samples 3 from distal assembly 133. For example, distal end 136 of lumen 135 may be configured to direct fluid from source of fluid 134 toward cavities 142, 152 of jaws 140, 150, respectively, so as to assist in dislodging tissue samples 3 therefrom. This may assist tissue removal device 70 in removing tissue samples 3 from tissue acquisition device 130 and into or onto any tissue removal device set forth herein. Any suitable fluid, such as saline, may be used in conjunction with tissue acquisition device 130.

According to another embodiment of the present invention, apparatus 1 may include tissue removal device 170. Examples of tissue removal device 170 are set forth in FIGS. 8-13. Tissue removal device 170 may include an elongate member 171, a proximal handle portion 172, a source of suction 173, a tissue sample storage device 174, and distal assembly 180. Source of suction 173 may be provided integrally with or independent of tissue sample storage device 174. Elongate member 171 may define a lumen 175 configured to accommodate suction, for example, from source of suction 173. Lumen 175 and/or source of suction 173 may also be in flow communication with storage device 174.

Distal assembly 180 may include an expandable portion 181, a collapsible rim 182, and a collapsible member 183. In an expanded configuration, at least a portion of expandable portion 181, collapsible rim 182, and/or collapsible member 183 may have a cross-sectional area larger than second lumen 12.

Expandable portion 181 may be expanded by any suitable means known in the art. For example, expandable portion 181 may be configured to be self-expanding. Alternatively, expandable portion 181 may be expanded mechanically by, for example, one or more tools and/or introduction of an expansion fluid. Expandable portion 181 may be configured to receive and/or store one or more tissue samples 3, and may be made out of any suitable biocompatible textile, film, sheet, or other material, for example, fluoropolymers (such as polytetrafluoroethylene (PTFE)) or Mylar. Expandable portion 181 may have a substantially funnel-like configuration when extended out of second lumen 12 of endoscope 10, however, in various embodiments expandable portion 181 may have any suitable shape, size, and/or configuration. For example, in some embodiments, expandable portion 181 may include cup-like formations. Expandable portion 181 may be connected to a distal portion 176 of elongate member 175 in any suitable manner using any suitable method, for example, adhesives, welding, and/or any known mechanical connection means. Expandable portion 181 may define a cavity 184 which may be in flow communication with source of suction 173 and/or storage device 174 via lumen 175 of elongate member 171, for example, to suction tissue samples 3 from cavity 184 into lumen 175 and/or storage device 174 via source of suction 173.

Collapsible rim 182 may be configured to expand expandable portion 181, for example, collapsible rim 182 may have a substantially circular shape so as to place expandable portion 181 into the funnel-like configuration. Collapsible rim 182 may be any suitable material that may be collapsible, yet may be rigid enough to retain its shape when expanded, for example, nitinol. Collapsible rim 182 may be made out of a biocompatible material, and may be retained at the outermost edge of expandable portion 181, for example, so as to form a substantially circular shape when fully expanded and assist in maintaining the funnel-like configuration of expandable portion 181. Expandable portion 181 and collapsible rim 182 may be connected in any suitable manner using any suitable method. For example, collapsible rim 182 may be connected to expandable portion 181 using adhesives and/or the edge of expandable portion 181 may be folded over collapsible rim 182.

Collapsible member 183 may be made of the same or different material as collapsible rim 182, for example, nitinol.

One end 185 of collapsible member 183 may be attached to elongate member 171 while the other end 186 of collapsible member 183 may be attached to at least one of collapsible rim 182 and/or expandable portion 181. For example, end 185 of collapsible member 183 may be attached to elongate member 171 using adhesives while end 186 may be attached to collapsible rim 182 via welding. Any other suitable connection method may be used. Collapsible member 183 may be attached to collapsible rim 182 and/or expandable portion 181 at a position substantially opposite of where elongate member 171 is attached to collapsible rim 182 and/or expandable portion 181.

Tissue removal device 170 may be keyed with respect to endoscope 10 such that tissue removal device 170 is in a proper position and orientation to receive tissue samples 3 from tissue acquisition device 30. For example, elongate member 171 and second lumen 12 may have a substantially ovular shape such that they may be rotationally aligned, as set forth in FIG. 13. Thus, collapsible member 183 may substantially face toward tissue acquisition device 30, and elongate member 171 may face away from tissue acquisition device 30, so as to allow tissue acquisition device 30 to be more easily placed in cavity 184.

Figure 8:
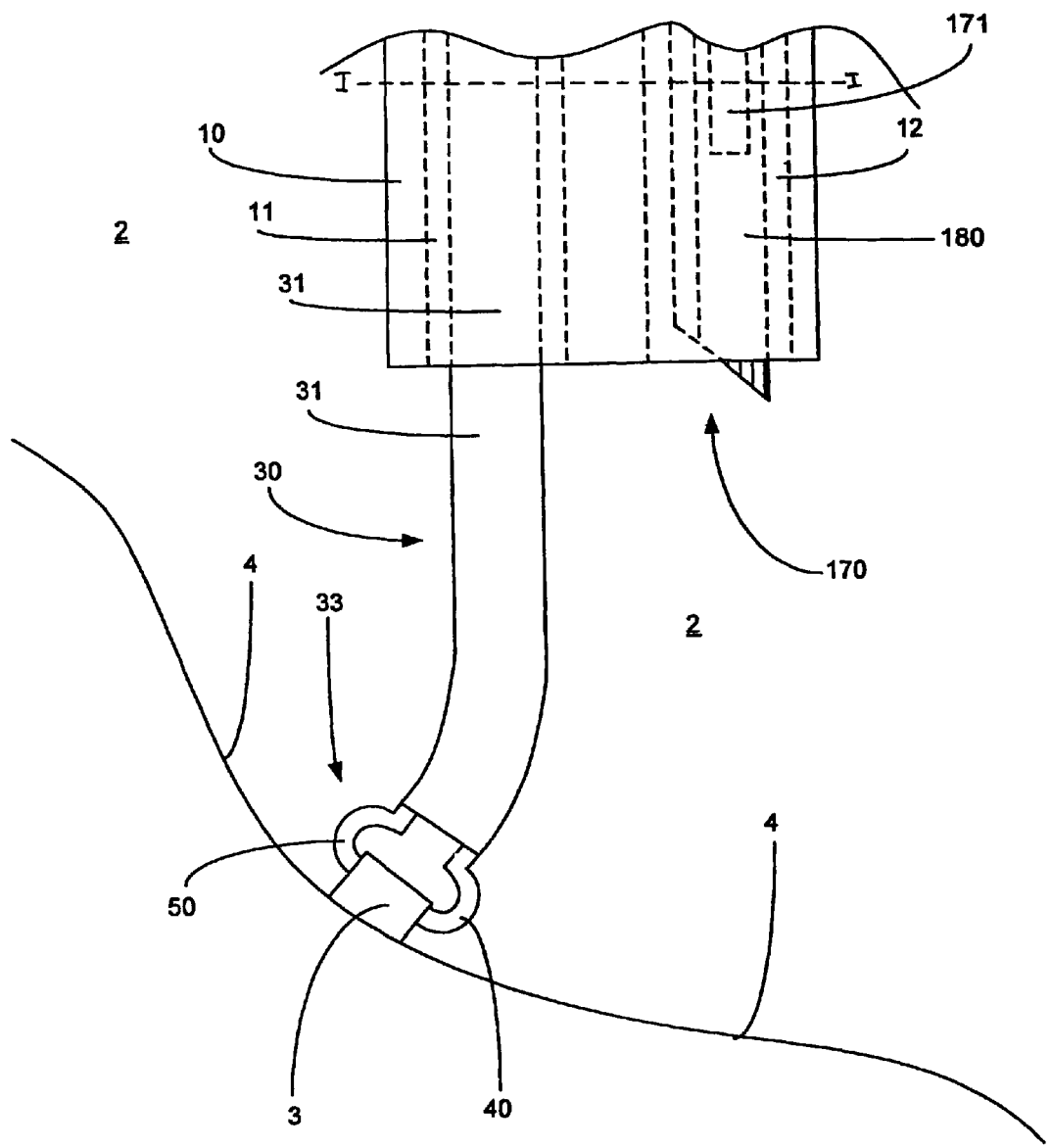
FIG. 8 is a schematic view of an apparatus, according to a yet further embodiment of the invention.
Figure 9:
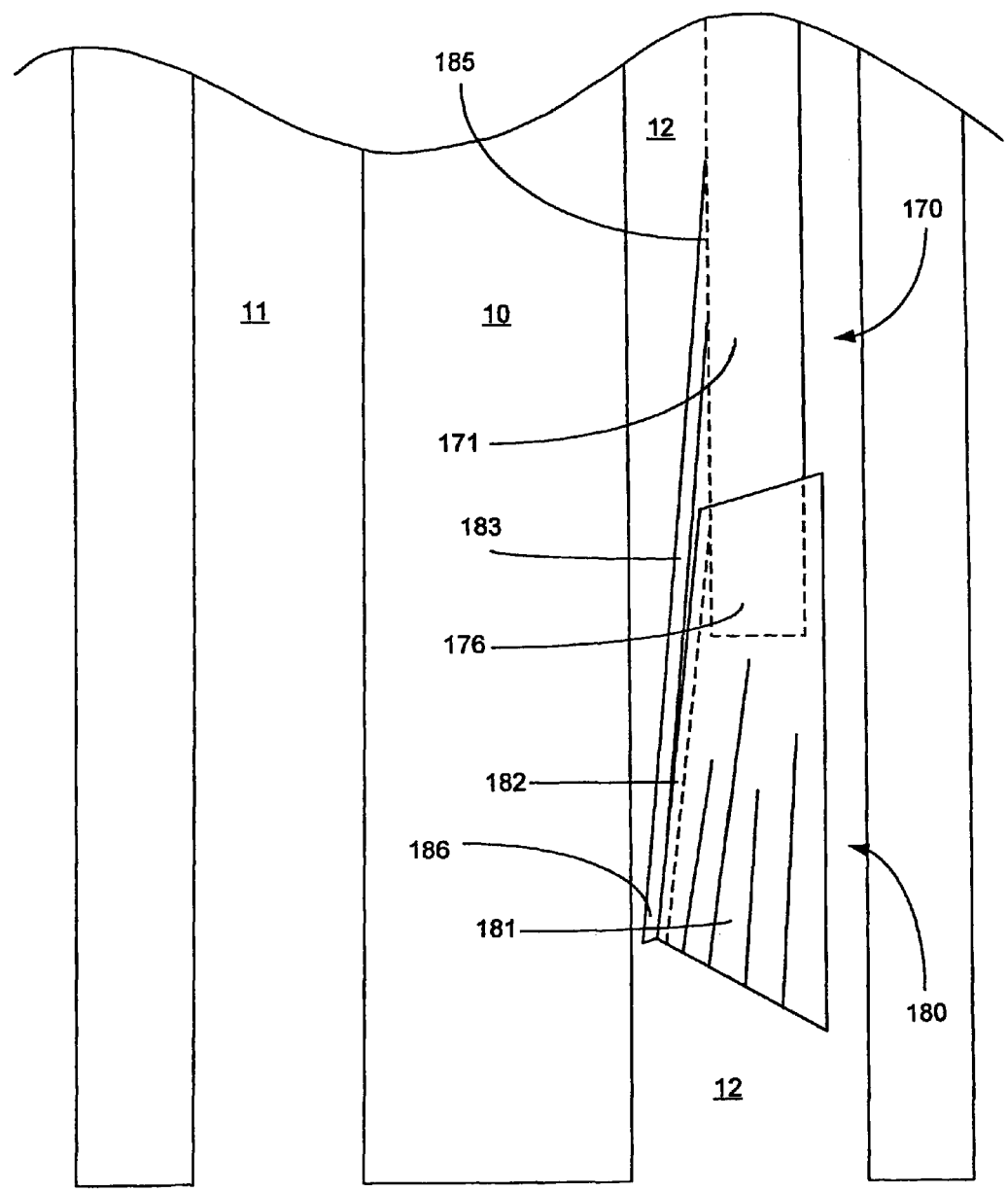
FIGS. 9-12 are schematic views of the apparatus of FIG. 8.
Figure 10:
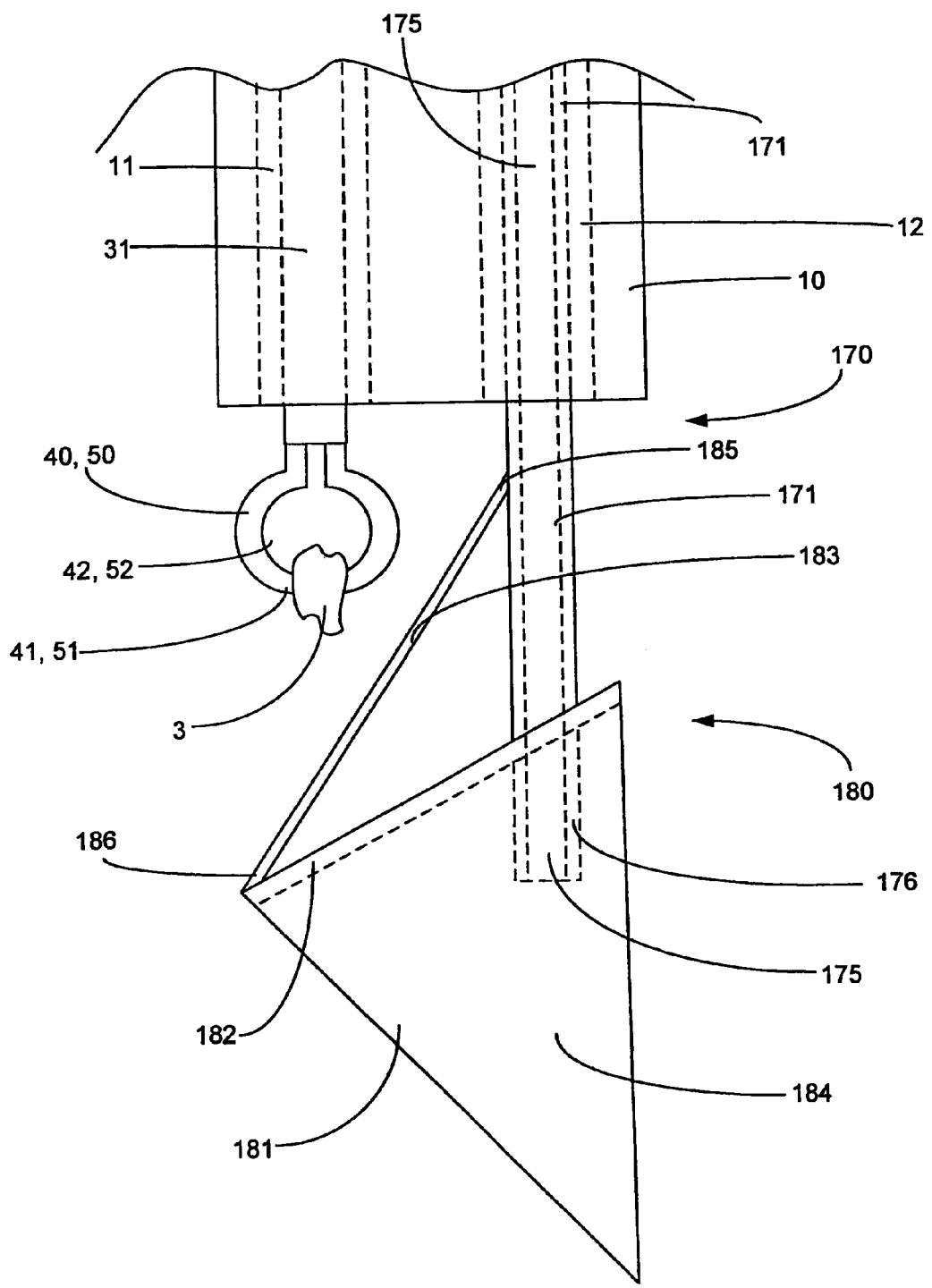
Figure 11:
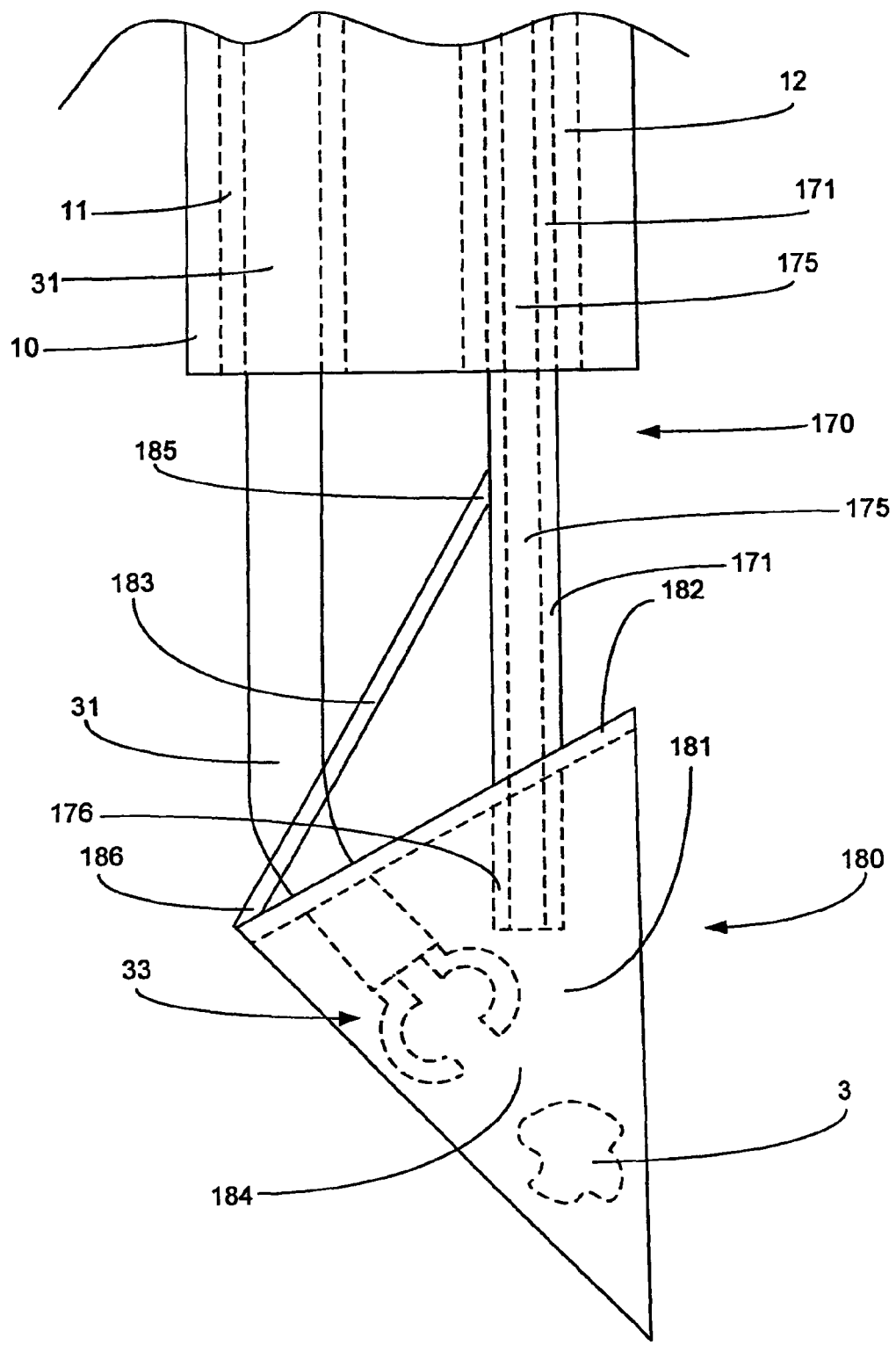
Figure 12:
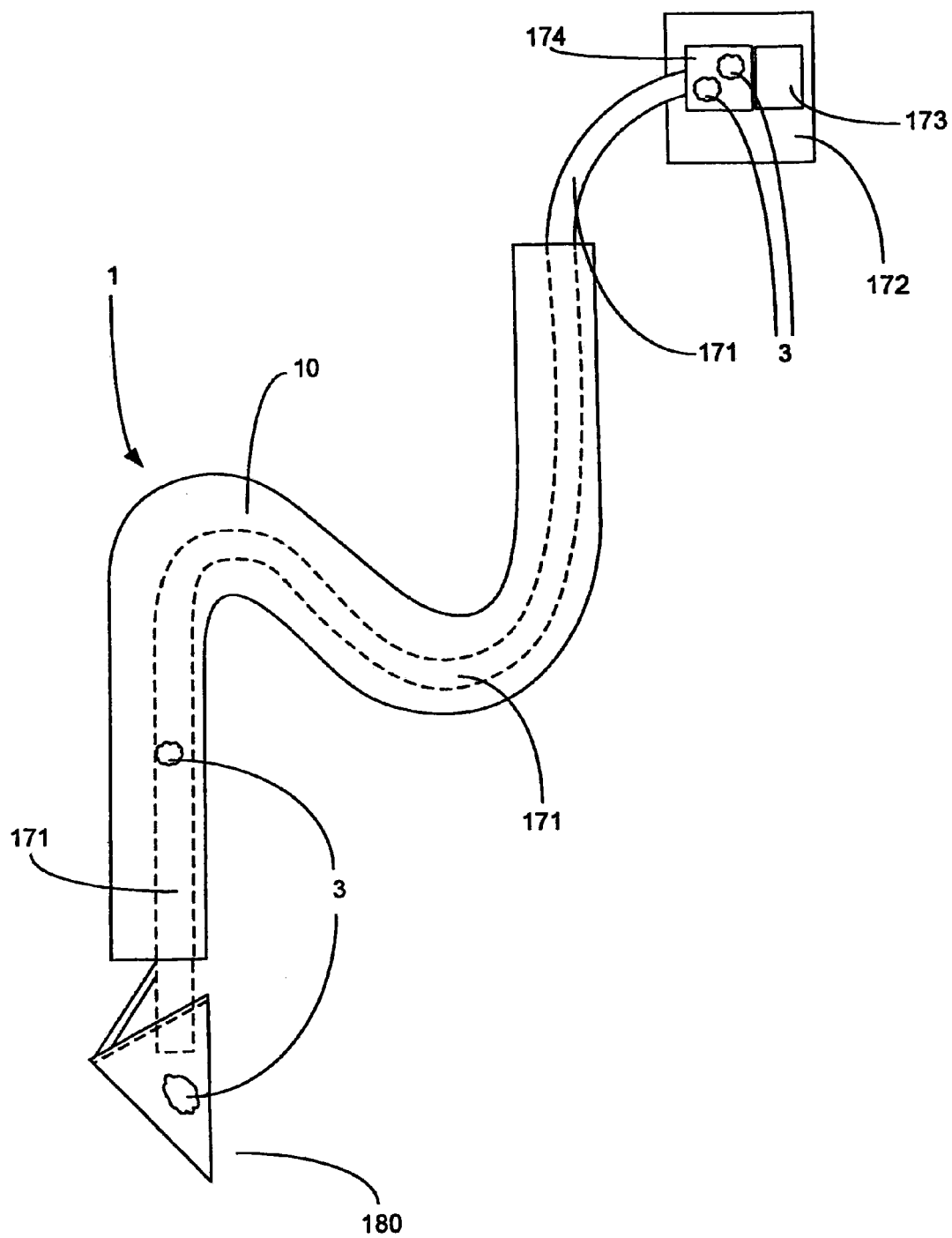
Figure 13:
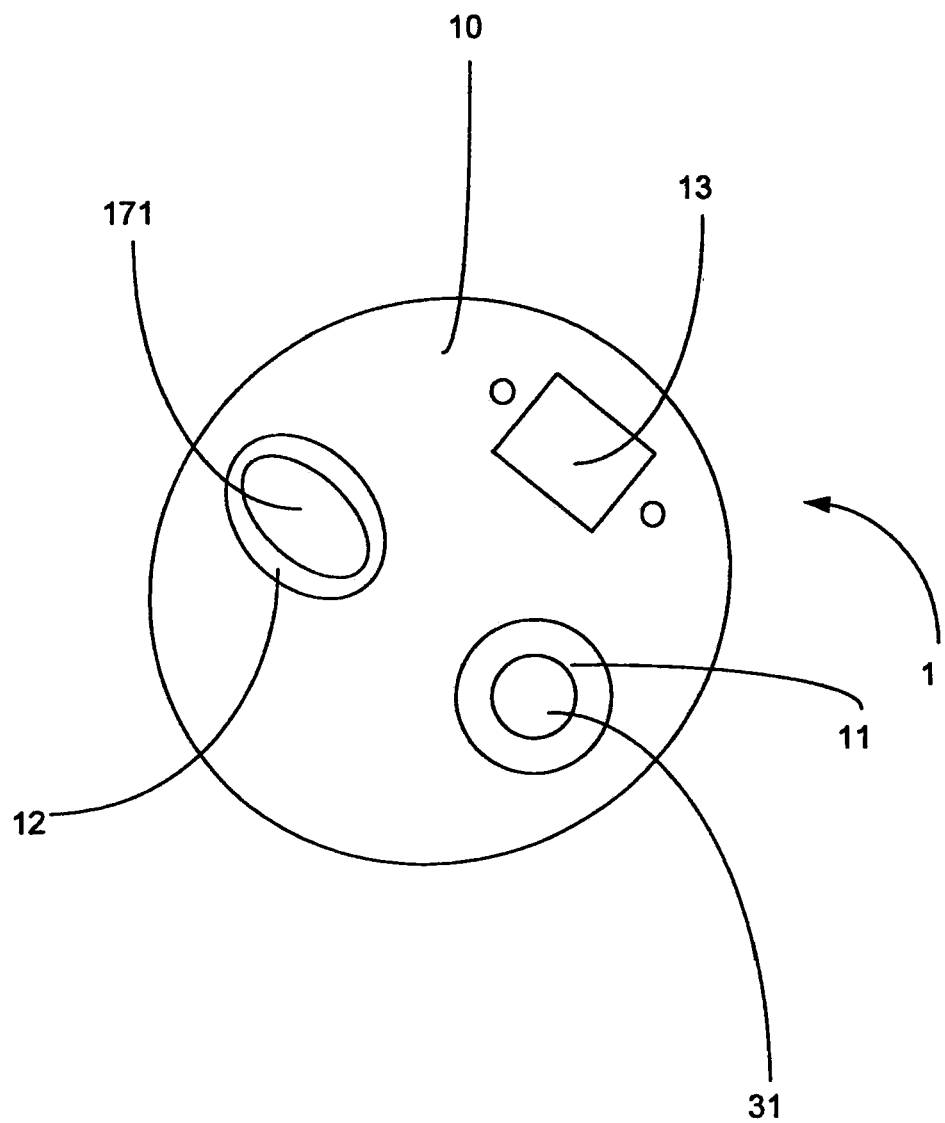
FIG. 13 is a cross-sectional view of the apparatus of FIG. 8 along line I-I set forth in FIG. 8.

Tissue removal device 170 may be used instead of any other previously described tissue removal device embodiments for any methods or method steps set forth herein. Tissue removal device 170 may be advanced through second lumen 12 in a substantially collapsed configuration, for example, as shown in FIGS. 8 and 9. In such a configuration, expandable portion 181, collapsible rim 182, and collapsible member 183 may be in a collapsed form within second lumen 12, for example, due to walls defining second lumen 12. Once distal assembly 180 is advanced distally past distal end 14 of endoscope 10, expandable portion 181, collapsible rim 182, and/or collapsible member 183 may expand such that cavity 184 increases in volume, for example, as shown in FIGS. 10-12. Depending on the rotational orientation of distal assembly 180 relative to tissue acquisition device 30, distal assembly 180 may be rotated so as to allow tissue acquisition device 30 to be more easily placed in cavity 184.

Once tissue sample 3 from tissue acquisition device 30 is placed in cavity 184 of expandable portion 181, for example, as shown in FIG. 11, suction from source of suction 173 may cause tissue sample 3 to enter the portion of lumen 175 defined by distal portion 176. Tissue sample 3 may then be placed into storage device 174, for example, as shown in FIG. 12. Tissue acquisition device 30 may place as many tissue samples 3 within cavity 184 to be suctioned through lumen 175 as desired.

Once the desired number of tissue samples 3 have been acquired, suctioned out of cavity 184, and/or placed in storage device 174, tissue removal device 170 may be advanced proximally out of second lumen 12. When tissue removal device 170 retracts within second lumen 12, as at least some of expandable portion 181 may have a larger cross-sectional area than second lumen 12, expandable portion 181, collapsible rim 182, and collapsible wire 183 may collapse such that distal assembly 180 fits into second lumen 12.

Figure 14:
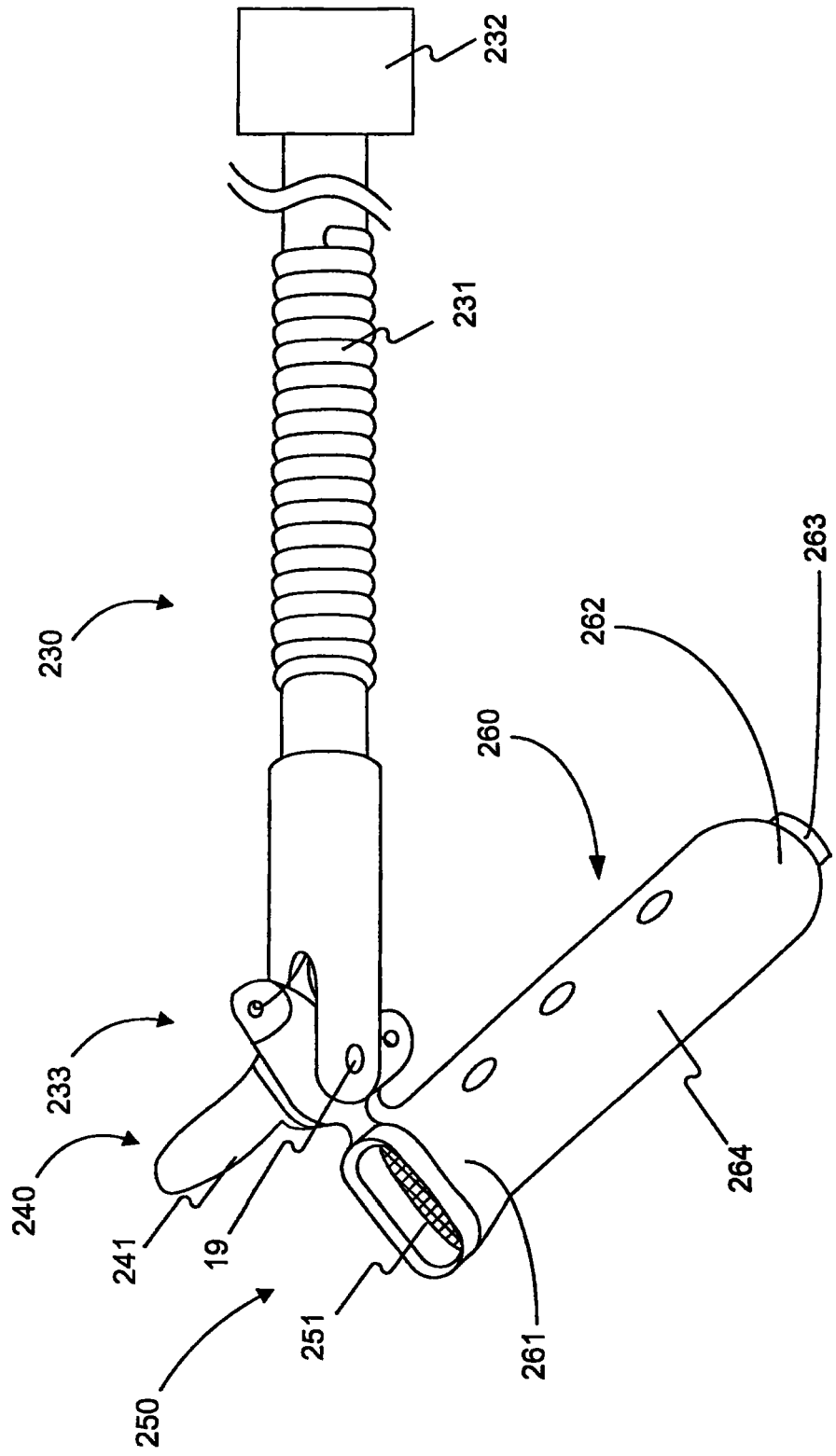
FIG. 14 is a schematic view of a tissue acquisition device.

According to another embodiment of the invention, apparatus 1 may include tissue acquisition device 230, an example of which is set forth in FIG. 14. Tissue acquisition device 230 may be used in place of any other previously described tissue acquisition device embodiments and related methods or method steps set forth herein. Tissue acquisition device 230 may include elongate member 231, handle portion 232, and distal assembly 233.

Distal assembly 233 may include jaws 240, 250. Jaws 240, 250 may be operably connected to one another by any suitable means known in the art. For example, jaws 240, 250 may be rotatably connected by, for example, pin 19. At least one of jaws 240, 250 may be connected to a storage device 260, which may be configured to store one or more tissue samples 3 acquired by jaws 240, 250. Examples of such tissue acquisition devices having a storage device may include those described in U.S. Pat. No. 7,118,586 B1 and U.S. Patent Application Publication Nos. 2005-0054945-A1 and 2005-0113867-A1, the entirety of all of which are incorporated herein by reference.

Jaws 240, 250 may be configured to acquire tissue samples 3 and urge them into chamber 264 defined by storage device 260. For example, first jaw 240 may include a protrusion 241 configured to urge tissue sample 3 into hole 251 of second jaw 250. Hole 251 may be in flow communication with proximal end 261 of storage chamber 264, such that tissue samples 3 are placed into storage chamber 264 via hole 251 and proximal end 261. Storage chamber 264 may have any suitable shape, size, and/or configuration. In some embodiments, for example, storage chamber 264 may include one or more portions that may be rigid, flexible, or combinations thereof.

Distal end 262 of storage device 260 may include an aperture 263. Aperture 263 may be in flow communication with storage chamber 264 and the outside environment, and may be configured such that tissue samples 3 cannot be forced out of storage chamber 264 via aperture 263 without an external force, for example, physical, fluid, and/or suction pressure. For example, aperture 263 may have a smaller cross-sectional area than that of chamber 264. Aperture 263 may be disposed on any portion of jaws 240, 250 and/or storage device 260.

According to another embodiment of the invention, apparatus 1 may include tissue removal device 270. Examples of tissue removal device 270 are set forth in FIGS. 15-19. Tissue removal device 270 may be used in place of any other previously-described tissue removal device embodiment and related methods or method steps set forth herein. Tissue removal device 270 may include elongate member 271, handle portion 272, source of suction 273, storage device 274, and distal assembly 280.

Elongate member 271 may define lumen 275. Lumen 275 may be in flow communication with source of suction 273, for example, via handle portion 272, and distal assembly 280. Distal assembly 280 may include a flexible portion 281 including a hole 282 in flow communication with source of suction 273, lumen 275, and/or storage device 274. Each of hole 282, lumen 275, storage device 274, and/or source of suction 273 may be configured to proximally suction tissue samples 3 from a position distal to distal assembly 280 to storage device 274 via lumen 275 and hole 282. For example, tissue samples 3 may be disposed in any tissue acquisition device set forth herein.

Flexible portion 281 may assist in placing tissue sample 3 adjacent to hole 282 such that tissue sample 3 enters hole 282 on its way to storage device 274 via lumen 275. For example, flexible portion 281 may have a funnel-like configuration which expands distally. Flexible portion 281 may be made of a flexible biocompatible material, for example, rubber or polymers. Flexible portion 281 may be configured to form a substantially fluid-tight seal with a desired surface when suction is applied through hole 282, for example, to assist in suctioning tissue samples 3 from any tissue acquisition device set forth herein.

In a first example, flexible portion 281 may be aligned with cavities 42, 52 of jaws 40, 50, such that tissue samples 3 from cavities 42, 52 are suctioned into hole 282.

In another example, flexible portion 281 may be placed around aperture 263 of tissue acquisition device 230 such that hole 282 and lumen 275 are in flow communication with storage chamber 264 via aperture 263. Such examples are shown in FIGS. 17 and 18. In such a configuration, suction force from source of suction 273 may be applied such that tissue samples 3 disposed in storage chamber 264 are suctioned into lumen 275 via aperture 263 and hole 282. Jaws 240, 250 of tissue acquisition device 230 may be closed, for example, to more easily allow a vacuum to form in storage chamber 264 and aid in moving tissue samples 3 from storage chamber 264 to lumen 275. Fluid may also be provided to storage chamber 264 using any suitable devices and/or methods to aid in such removal.

Figure 19:
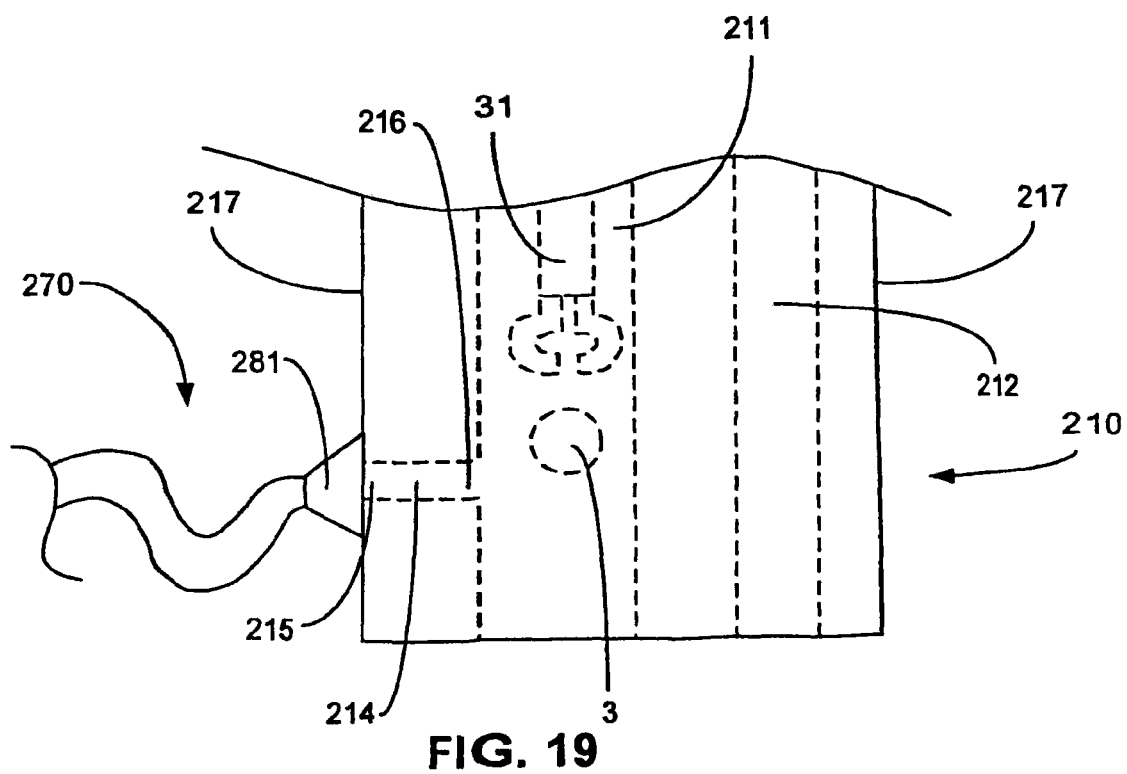
FIG. 19 is a schematic view of an apparatus, according to a further embodiment of the invention.

In a further example, flexible portion 281 may be placed around external end 215 of auxiliary lumen 214 of endoscope 210, for example, as shown in FIG. 19. Flexible portion 281 may form a substantially fluidtight seal with outer surface 217 of endoscope 210. Auxiliary lumen 214 may be in flow communication with first lumen 211 via internal end 216 of auxiliary lumen 214. First lumen 211 may be configured to accommodate any tissue acquisition device set forth herein. Tissue removal device 270 may be advanced into GI tract 2 such that flexible portion 281 is placed adjacent to external end 215 of auxiliary lumen 214 using any suitable method. For example, tissue removal device 270 may be advanced through second lumen 212. In another example, tissue removal device 270 may be advanced completely separately from endoscope 10, for example, from an end of the GI tract 2 opposite endoscope 10. In a further example, tissue removal device 270 may be advanced through a lumen of an external housing, for example, working lumen 313 of external housing 312 as set forth in FIG. 17.

After a tissue acquisition device, for example, tissue acquisition device 30, acquires tissue sample 3, distal assembly 33 including tissue sample 3 may be advanced proximally into first lumen 211. Distal assembly 33 may then eject tissue sample 3, for example, by opening jaws 40, 50. Tissue sample 3 may thus be disposed in first lumen 211 adjacent to proximal end 216 of auxiliary lumen 214. Source of suction 273 may then cause at least some vacuum in distal assembly 280, which may cause flexible portion 281 to form a substantially fluidtight seal with outer surface 217 around external end 215 of auxiliary lumen 214. Accordingly, at least some vacuum may also be formed in auxiliary lumen 214 and into at least a portion of first lumen 211. Due to this vacuum, tissue sample 3 may be pulled toward internal end 216, into auxiliary lumen 214, into hole 282, and into storage device 273 via lumen 275. To aid in moving tissue sample 3 toward internal end 216, fluid may be sent through first lumen 211 either from a source of fluid connected to first lumen 211, or a source of fluid connected to tissue acquisition device 30, for example, tissue acquisition device 130 shown in FIG. 7.

An apparatus may include an endoscope 310 including only one working lumen 311 configured to accommodate a medical device, for example, any one of a tissue acquisition device and a tissue removal device set forth herein. An example of such an apparatus is set forth in FIG. 17. The apparatus may also include an external housing 312 which is structurally separate from endoscope 310. External housing 312 may include a working lumen 313 configured to accommodate a medical device, for example, the other of the tissue acquisition device and tissue removal device not disposed in working lumen 311. In an example, tissue acquisition device 230 may be disposed in working lumen 311 and tissue removal device 270 may be disposed in working lumen 313, for example, as shown in FIG. 17. External housing 312 may have a substantially elongate configuration, may run substantially parallel to endoscope 310 along at least a portion of its length, and may be attached to an outer surface 314 of endoscope 310 in any suitable manner, for example, by a clamp, band, sheath, wrapping, cap, and/or an adhesive. External housing 312 may be permanently or selectively attached to endoscope 310, or not attached to endoscope 310.

Although the depicted embodiments of endoscope 310 and external housing 312 include one working lumen each, endoscope 310 and external housing 312 may include any suitable number of working lumens. Further, it is contemplated that any number of the disclosed devices may be advanced through either of endoscope 310 or external housing 312. For example, in one embodiment, two tissue acquisition devices 230 may be disposed within lumens of endoscope 310, and two removal tissue removal devices 270 may be disposed within lumens of external housing 312.

In various embodiments, any of the endoscopes 110, 210, 310 set forth herein may be used with any tissue acquisition device 30, 130, 230 and/or any tissue removal device 70, 170, 270 in any combination. Every elongate member set forth herein may be made of a suitable biocompatible material and may be flexible, for example, to traverse tortuous anatomy in the body. Any aspect set forth in any embodiment may be used with any other embodiment set forth herein. Every device and apparatus set forth herein may be tailored for desired intended uses. For example, the disclosed devices and apparatus may include one or more portions that are flexible, rigid, and/or combinations thereof. Additionally, every device and apparatus set forth herein may be used in any suitable medical procedure, may be selectively steerable so as to be advanced through any suitable body lumen and body cavity, and may be used to acquire and remove tissue from any suitable body portion. For example, the apparatuses and methods described herein may be used in any natural body lumen or tract, including those accessed orally, vaginally, or rectally. In addition, the apparatuses and methods can be used for tissue biopsy, stone removal, or any other retrieval of a biological or foreign substance from within the body. Moreover, the tissue acquisition device may be any suitable medical device and may include, but is not limited to, forceps, needles, snares, graspers, scoops, coring devices, wire loops, and/or baskets. Furthermore, the described tissue removal device may include, but is not limited to, suction devices and/or a secondary tissue acquisition device operating as a tissue removal device. In particular, it is contemplated that, in some embodiments, two or more tissue acquisition devices may operate interchangeably as tissue acquisition and tissue removal devices. Still further, the principles of the present disclosure provide for any number of tissue acquisition device 30, 130, 230 and/or any number of tissue removal device 70, 170, 270, in any suitable combination. For example, in some instances, three of the disclosed tissue acquisition devices may be used with two of the disclosed tissue removal devices.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An apparatus, comprising:
an endoscope including a first lumen and a second lumen;
an elongate member disposed in the first lumen and defining a working lumen and a fluid lumen; and
a tissue acquisition device disposed in the working lumen and a tissue removal device disposed in the second lumen, both the tissue acquisition device and the tissue removal device being moveable relative to the endoscope, wherein the tissue removal device includes an elongate member defining a suction lumen, and wherein an expandable distal assembly is coupled to the tissue removal device and configured to be in a collapsed configuration in the second lumen and in an expanded configuration in a body lumen, the expandable distal assembly being configured to accommodate both the tissue removal device and a distal assembly of the tissue acquisition device in the expanded configuration, wherein the tissue acquisition device is configured to acquire a tissue sample from the body lumen and selectively control the tissue sample when the tissue sample is unattached from the body lumen, and the tissue removal device is configured to capture the tissue sample when the tissue sample is unattached from the body lumen and to remove the tissue sample from the tissue acquisition device.

2. The apparatus of claim 1, wherein the tissue acquisition device is a biopsy forceps.

3. The apparatus of claim 2, wherein the suction lumen is configured to suction the tissue sample from the biopsy forceps.

4. The apparatus of claim 1, wherein the tissue acquisition device defines a fluid lumen for flow communication with a source of fluid, the fluid lumen being configured to accommodate fluid flow to dislodge the tissue sample from the tissue acquisition device.

5. The apparatus of claim 4, wherein the tissue acquisition device includes at least one jaw defining a cavity, and the fluid lumen is configured to accommodate fluid flow to dislodge the tissue sample from the cavity.

6. The apparatus of claim 1, wherein the tissue acquisition device is longitudinally moveable relative to the elongate member, and the fluid lumen is in communication with a source of fluid to accommodate fluid flow.

7. The apparatus of claim 6, wherein the fluid flow is configured to dislodge a tissue sample from a distal assembly of the tissue acquisition device.

8. The apparatus of claim 6, wherein the tissue acquisition device includes at least one jaw defining a cavity, and the fluid lumen of the elongate member is configured to accommodate fluid flow to dislodge the tissue sample from the cavity.

9. The apparatus of claim 1, further comprising a source of suction and a storage device, wherein the source of suction and the storage device are in flow communication with the suction lumen.

10. The apparatus of claim 9, wherein the tissue removal device includes a distal assembly including a flexible portion that extends radially and distally away from the distal assembly, the flexible portion surrounding a distal end of the suction lumen, wherein the suction lumen is configured to suction the tissue sample from the tissue acquisition device to the storage device.

11. The apparatus of claim 10, wherein the flexible portion is configured to form a substantially airtight seal with at least one of an outer surface of the endoscope and the storage device of the tissue acquisition device.

12. The apparatus of claim 1, wherein the suction lumen is configured to suction the tissue sample from the expandable distal assembly to a storage device.

13. The apparatus of claim 12, wherein the expandable distal assembly is self-expanding.

14. The apparatus of claim 12, wherein the expandable distal assembly includes an expandable portion defining a cavity configured to accommodate both the tissue sample and the distal assembly of the tissue acquisition device, and a collapsible rim defining a proximal edge of the expandable portion.

15. The apparatus of claim 14, wherein the expandable distal assembly further includes a collapsible member connected to the collapsible rim and the elongate member.

16. The apparatus of claim 14, wherein an opening of the cavity, configured to allow passage of both the tissue sample and the distal assembly of the acquisition device therethrough, is disposed on a proximal portion of the expandable portion.

17. The apparatus of claim 1, wherein an elongate portion of each of the tissue removal device and the second lumen are configured to prevent rotational movement relative to each other.

18. The apparatus of claim 17, wherein the elongate portions of the tissue removal device and the second lumen are keyed to each other.

19. An apparatus, comprising:
an endoscope having a proximal end and a distal end;
a first elongate member having a distal end and defining a suction lumen configured to be in flow communication with a source of suction;
a tissue acquisition device having a distal assembly, the tissue acquisition device configured to be movable relative to the endoscope;
an expandable distal assembly coupled to the first elongate member and configured to be in a collapsed configuration in a lumen of the endoscope and in an expanded configuration in a body lumen, the expandable distal assembly being configured to contain a tissue sample, a distal end of the suction lumen, and the distal assembly of the tissue acquisition device when in the expanded configuration,
wherein the source of suction is configured to suction the tissue sample from the expandable distal assembly via the suction lumen.

20. The apparatus of claim 19, wherein the expandable distal assembly is self-expanding.

21. The apparatus of claim 19, further comprising a storage device in flow communication with the suction lumen, at least one of the source of suction and the storage device being located outside of the body lumen.

22. The apparatus of claim 19, wherein the expandable distal assembly includes an expandable portion defining a cavity configured to accommodate the tissue sample, the distal end of the first elongate member, and the distal assembly of the tissue acquisition device, and a collapsible rim defining a proximal edge of the expandable portion.

23. The apparatus of claim 22, wherein the expandable distal assembly further includes a collapsible member connected to the collapsible rim and the first elongate member.

24. The apparatus of claim 22, wherein an opening of the cavity, configured to allow passage of the tissue sample, the distal end of the first elongate member, and the distal assembly of the acquisition device therethrough, is disposed on a proximal portion of the expandable portion.

25. The apparatus of claim 19, wherein the first elongate member and the lumen of the endoscope are keyed to prevent rotational movement relative to each other.

26. The apparatus of claim 19,
wherein the first elongate member and the tissue acquisition device are at least partially disposed in a lumen of the endoscope.

27. The apparatus of claim 26, wherein the endoscope includes a second lumen different from the lumen, wherein the tissue acquisition device is disposed in the second lumen of the endoscope, the tissue acquisition device being moveable relative to the endoscope.

28. The apparatus of claim 19, wherein a distal end of the expandable distal assembly is closed.

29. The apparatus of claim 19, further comprising a second elongate member disposed within a second lumen of the endoscope different from the lumen of the endoscope; wherein the second elongate member includes a third lumen and a fourth lumen, and the tissue acquisition device is disposed within one of the third lumen and the fourth lumen of the second elongate member.

30. An apparatus, comprising:
an endoscope including a first lumen configured to accommodate a tissue acquisition device or a tissue removal device, wherein the tissue acquisition device is configured to acquire a tissue sample from a body lumen and control the tissue sample when unattached from the body lumen, and the tissue removal device includes a suction lumen;
an elongate member including a working lumen configured to accommodate the tissue acquisition device or the tissue removal device;
one of the tissue acquisition device and the tissue removal device being disposed in the first lumen and the other of the tissue removal device and the tissue acquisition device being disposed in the working lumen, both the tissue acquisition device and the tissue removal device being moveable relative to the endoscope and the elongate member; and
an expandable distal assembly coupled to the tissue removal device and configured to extend beyond a distal end of the endoscope and surround a distal end of the tissue acquisition device and a distal end of the tissue removal device.

31. The apparatus of claim 30, wherein the elongate member is attached to the endoscope at least along a portion of its length.

32. The apparatus of claim 30, wherein the elongate member is completely unattached to the endoscope.

33. The apparatus of claim 30, wherein the elongate member is moveable relative to the endoscope.

34. The apparatus of claim 30, wherein the endoscope includes a second lumen and the elongate member is disposed within the second lumen.

35. The apparatus of claim 30, wherein the elongate member further defines a fluid lumen.

36. The apparatus of claim 30, wherein a distal end of the expandable distal assembly is closed.

* * * * *